US006424369B1

(12) United States Patent
Adair et al.

(10) Patent No.: US 6,424,369 B1
(45) Date of Patent: Jul. 23, 2002

(54) HAND-HELD COMPUTERS INCORPORATING REDUCED AREA IMAGING DEVICES

(76) Inventors: Edwin L. Adair, 317 Paragon Way, Castle Pines, CO (US) 80104; Jeffrey L. Adair, 1861 E. Redfox Pl., Highlands, CO (US) 80126; Randall S. Adair, 3082 S. Flamingo Way, Denver, CO (US) 80222

(*) Notice: Subject to any disclaimer, the term of this patent is extended or adjusted under 35 U.S.C. 154(b) by 45 days.

(21) Appl. No.: 09/638,976

(22) Filed: Aug. 15, 2000

Related U.S. Application Data

(63) Continuation-in-part of application No. 09/496,312, filed on Feb. 1, 2000, which is a continuation of application No. 09/175,685, filed on Oct. 20, 1998, now Pat. No. 6,043,839, which is a continuation-in-part of application No. 08/944,322, filed on Oct. 6, 1997, now Pat. No. 5,929,901.

(51) Int. Cl.[7] ................................................. H04N 7/18
(52) U.S. Cl. ........................ 348/76; 348/376; 455/566; 455/556
(58) Field of Search ........................ 348/76–80, 10–18, 348/69–75, 158, 373, 376; 455/556, 566, 346, 345

(56) References Cited

U.S. PATENT DOCUMENTS

| | | | |
|---|---|---|---|
| 4,491,865 A | 1/1985 | Danna et al. | 358/98 |
| 4,745,471 A | 5/1988 | Takamura et al. | 358/98 |
| 4,786,965 A | 11/1988 | Yabe | 358/98 |
| 4,814,648 A | 3/1989 | Hynecek | 307/497 |
| 4,854,302 A | 8/1989 | Allred, III | 128/6 |
| 4,869,246 A | 9/1989 | Adair | 128/303.1 |
| 4,928,300 A | 5/1990 | Ogawa et al. | 379/53 |
| 4,942,473 A | 7/1990 | Zeevi et al. | 348/76 |
| RE33,854 E | 3/1992 | Adair | 128/6 |
| 5,116,317 A | 5/1992 | Carson, Jr. et al. | 604/96 |

(List continued on next page.)

FOREIGN PATENT DOCUMENTS

| | | |
|---|---|---|
| EP | 0 492 349 A1 | 7/1992 |
| EP | 0 957 448 A2 | 11/1999 |
| WO | WO 97/26744 | 7/1997 |

OTHER PUBLICATIONS

"Active–Pixel Image Sensor Integrated With Readout Circuits", *NASA Tech Briefs*, Oct. 1996.
"NASA's Tiny Camera Has a Wide–Angle Future", *Business Week*, Mar. 6, 1995.

(List continued on next page.)

*Primary Examiner*—Andy Rao
(74) *Attorney, Agent, or Firm*—Sheridan Ross P.C.

(57) ABSTRACT

A reduced area imaging device is provided for use with a miniature hand-held computer referred to in the industry as a PDA. In one configuration of the imaging device, the image sensor is placed remote from the remaining image processing circuitry. In a second configuration, all of the image processing circuitry to include the image sensor is placed in a stacked fashion near the same location. In the first configuration, the entire imaging device can be placed at the distal end of a camera module. In a second configuration, the image sensor is remote from the remaining image processing circuitry wherein available space within the PDA is used to house the remaining circuitry. In any of the embodiments, the image sensor may be placed alone on a first circuit board, or timing and control circuits may be included on the first circuit board containing the image sensor. One or more video processing boards can be stacked in a longitudinal fashion with respect to the first board, or the video processing boards may be placed within the housing of the communication device. The PDA includes a miniature LCD-type video view screen which is capable of viewing not only the images taken by the camera module, but also can show incoming video images received from a personal computer connected to a global communications network. The camera module is of such small size that it can be easily stored within the housing of the PDA, and may be attached thereto as by a small retractable cable.

75 Claims, 12 Drawing Sheets

U.S. PATENT DOCUMENTS

| | | | |
|---|---|---|---|
| 5,162,913 A | 11/1992 | Chatenever et al. | 358/209 |
| 5,220,198 A | 6/1993 | Tsuji | 257/731 |
| 5,251,613 A | 10/1993 | Adair | 128/6 |
| 5,381,784 A | 1/1995 | Adair | 128/6 |
| 5,402,768 A | 4/1995 | Adair | 128/4 |
| 5,453,785 A | 9/1995 | Lenhardt et al. | 348/357 |
| 5,471,515 A | 11/1995 | Fossum et al. | 377/60 |
| 5,489,256 A | 2/1996 | Adair | 600/133 |
| 5,605,531 A | 2/1997 | Lane et al. | 600/118 |
| 5,630,782 A | 5/1997 | Adair | 600/133 |
| 5,630,783 A | 5/1997 | Steinberg | 600/158 |
| 5,682,199 A | 10/1997 | Lankford | 348/72 |
| 5,701,155 A | 12/1997 | Wood et al. | 348/72 |
| 5,734,418 A | 3/1998 | Danna | 348/76 |
| 5,748,441 A | 5/1998 | Loritz et al. | 361/683 |
| 5,754,313 A | 5/1998 | Pelchy et al. | 348/76 |
| 5,801,919 A | 9/1998 | Griencewic | 361/683 |
| 5,900,875 A | 5/1999 | Haitani et al. | 345/349 |
| 5,929,901 A | 7/1999 | Adair et al. | 348/76 |
| 5,983,073 A | 11/1999 | Ditzik | 455/11.1 |
| 6,009,336 A * | 12/1999 | Harris et al. | 455/566 |
| 6,018,670 A | 1/2000 | Degenhardt | 455/561 |
| 6,067,313 A | 5/2000 | Cafarella et al. | 375/130 |
| 6,073,034 A * | 6/2000 | Jacobsen et al. | 455/566 |
| 6,083,353 A * | 7/2000 | Alexander et al. | 202/158 |
| 6,104,334 A * | 8/2000 | Allport | 341/175 |
| 6,141,037 A * | 10/2000 | Upton et al. | 348/65 |
| 6,147,366 A * | 11/2000 | Drottar et al. | 257/82 |
| 6,184,804 B1 * | 2/2001 | Harrison | 341/22 |

OTHER PUBLICATIONS

"Imaging Options Expand With CMOS Technology", *Laser Focus World*, Jun. 1997.

"Applications Hold the Key to Imager Choice", *Photonics Spectra*, Mar. 1997.

"CMOS Image Sensors Challenge CCDs", Microdesign Resources, Jun. 22, 1998, Microprocessor Report, pp. 1–5.

"Silicon Eyes", Business Week, pp. 94–100, Oct. 12, 1998.

* cited by examiner

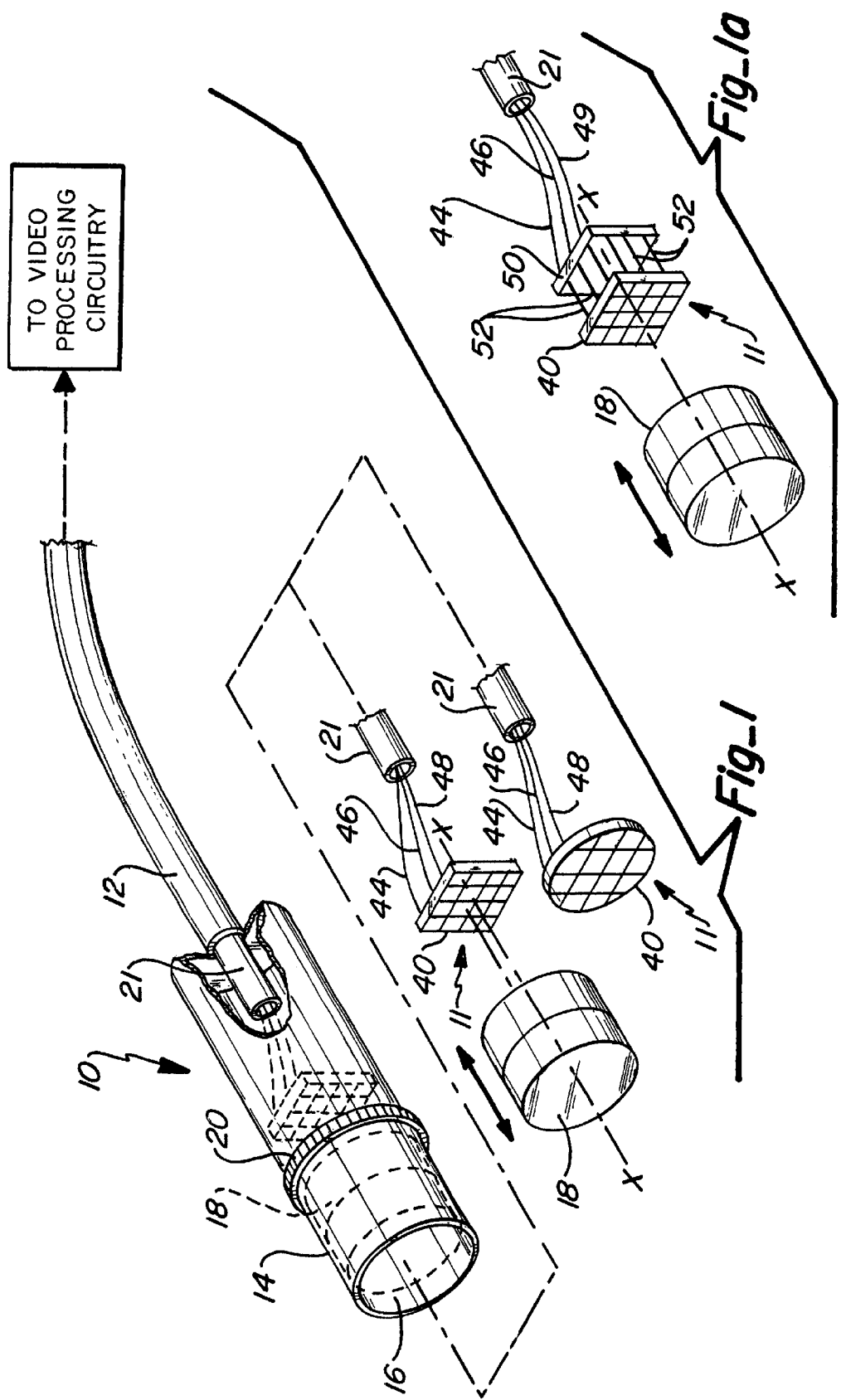

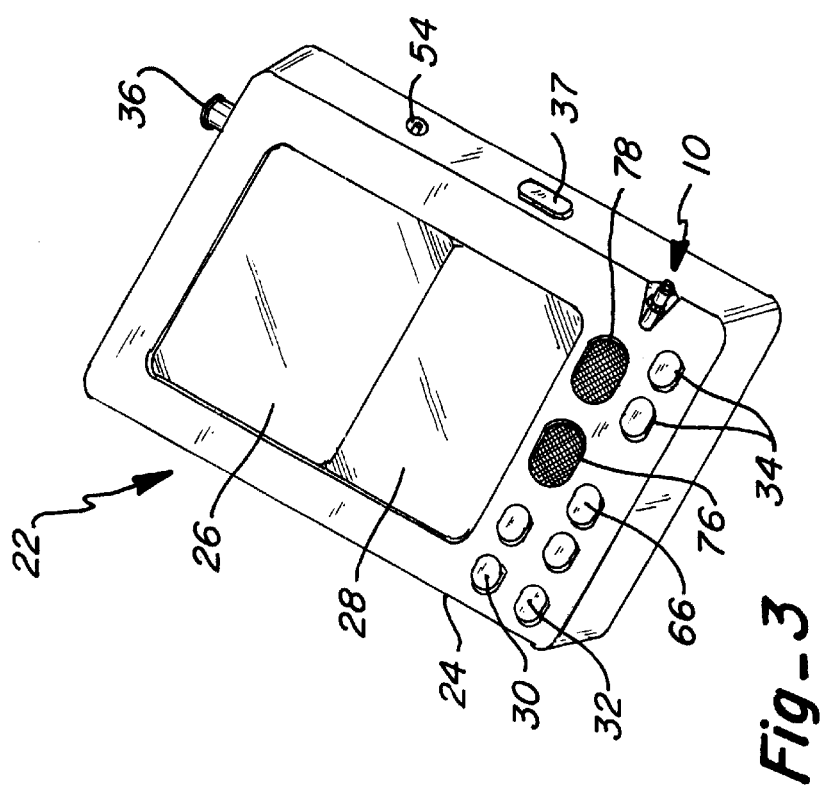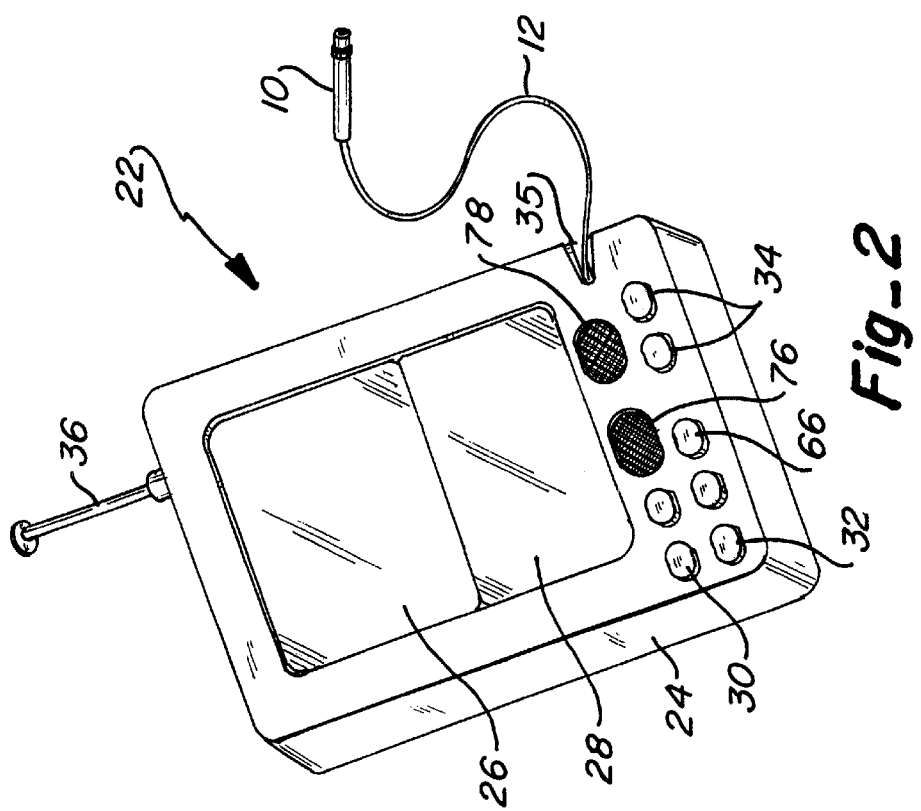

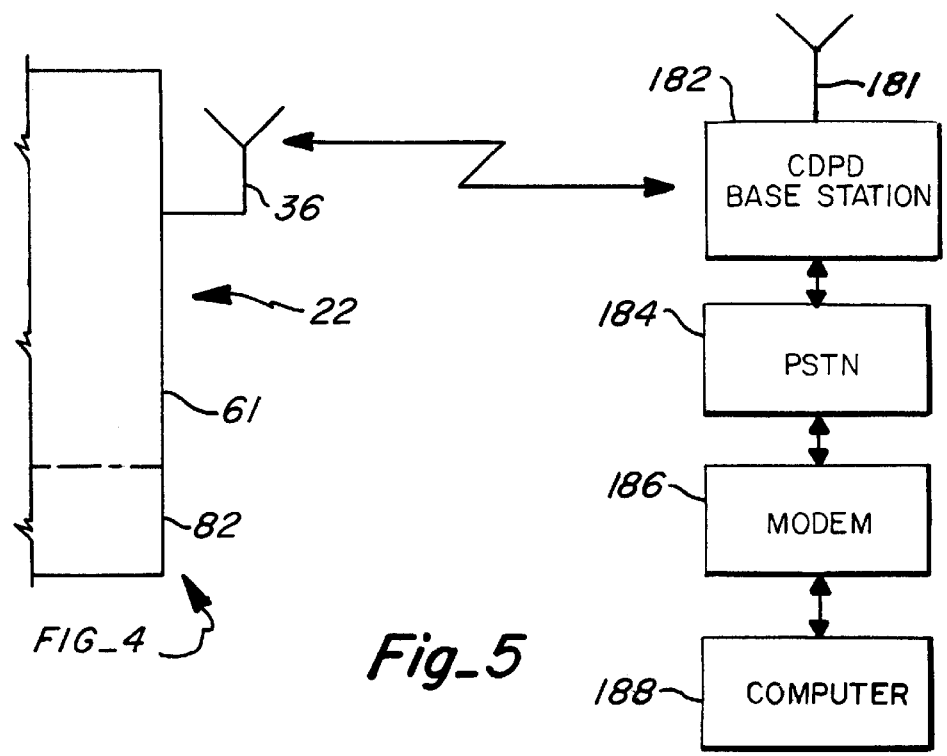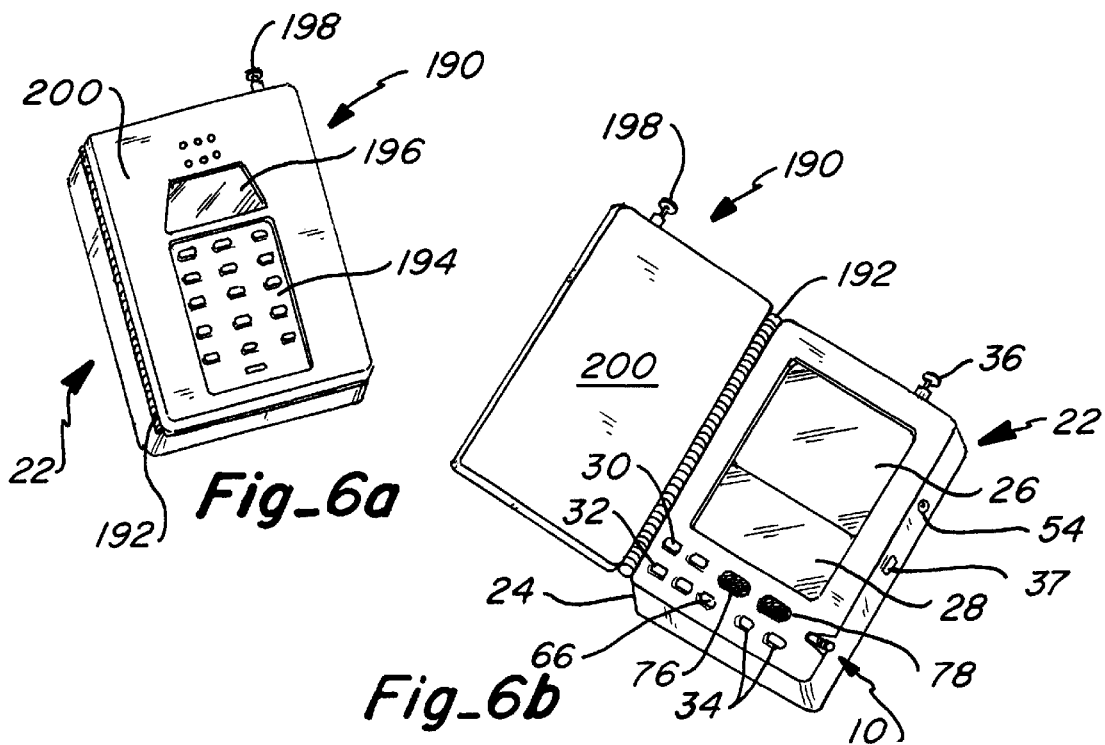

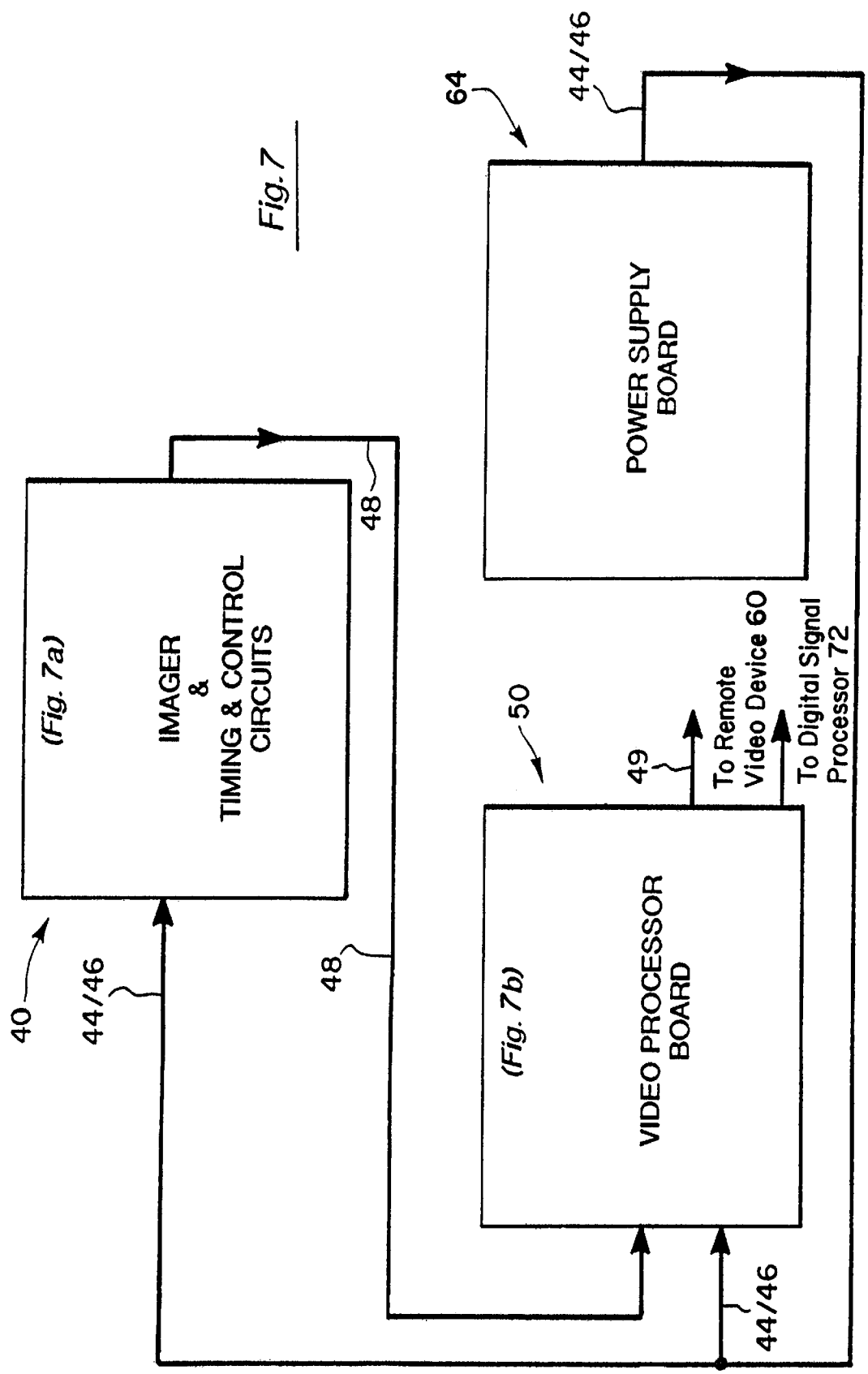

HAND-HELD COMPUTERS INCORPORATING REDUCED AREA IMAGING DEVICES

This application is a continuation-in-part of U.S. Ser. No. 09/496,312, filed Feb. 1, 2000, and entitled "Reduced Area Imaging Devices", which is a continuation application of U.S. Ser. No. 09/175,685, filed Oct. 20, 1998 and entitled "Reduced Area Imaging Devices", now U.S. Pat. No. 6,043, 839, which is a continuation-in-part of U.S. Ser. No. 08/944, 322, filed Oct. 6, 1997 and entitled "Reduced Area Imaging Devices Incorporated Within Surgical Instruments", now U.S. Pat. No. 5,929,901.

TECHNICAL FIELD

This invention relates to solid state image sensors and associated electronics, and more particularly, to solid state image sensors which are configured to be of a minimum size and used within miniature computer systems known as palm top computers, personal digital assistants (PDA), or hand-held computers/organizers.

BACKGROUND ART

The three most common solid state image sensors include charged coupled devices (CCD), charge injection devices (CID) and photo diode arrays. In the mid-1980s, complementary metal oxide semiconductors (CMOS) were developed for industrial use. CMOS imaging devices offer improved functionality and simplified system interfacing. Furthermore, many CMOS imagers can be manufactured at a fraction of the cost of other solid state imaging technologies.

The CCD device is still the preferred type of imager used in scientific applications. Only recently have CMOS-type devices been improved such that the quality of imaging compares to that of CCD devices. However, there are enormous drawbacks with CCD devices. Two major drawbacks are that CCD device have immense power requirements, and the amount of processing circuitry required for a CCD imager always requires the use of a remote processing circuitry module which can process the image signal produced by the CCD imager. Also, because of the type of chip architecture used with CCD devices, on-chip processing is impossible. Therefore, even timing and control circuitry must be remoted from the CCD imager plane. Therefore, CCD technology is the antithesis of "camera on a chip" technology discussed below.

One particular advance in CMOS technology has been in the active pixel-type CMOS imagers which consist of randomly accessible pixels with an amplifier at each pixel site. One advantage of active pixel-type imagers is that the amplifier placement results in lower noise levels. Another major advantage is that these CMOS imagers can be mass produced on standard semiconductor production lines. One particularly notable advance in the area of CMOS imagers including active pixel-type arrays is the CMOS imager described in U.S. Pat. No. 5,471,515 to Fossum, et al. This CMOS imager can incorporate a number of other different electronic controls that are usually found on multiple circuit boards of much larger size. For example, timing circuits, and special functions such as zoom and anti-jitter controls can be placed on the same circuit board containing the CMOS pixel array without significantly increasing the overall size of the host circuit board. Furthermore, this particular CMOS imager requires 100 times less power than a CCD-type imager. In short, the CMOS imager disclosed in Fossum, et al. has enabled the development of a "camera on a chip."

Passive pixel-type CMOS imagers have also been improved so that they too can be used in an imaging device which qualifies as a "camera on a chip." In short, the major difference between passive and active CMOS pixel arrays is that a passive pixel-type imager does not perform signal amplification at each pixel site. One example of a manufacturer which has developed a passive pixel array with performance nearly equal to known active pixel devices and compatible with the read out circuitry disclosed in the U.S. Pat. No. 5,471,515 is VLSI Vision, Ltd., 1190 Saratoga Avenue, Suite 180, San Jose, Calif. 95129. A further description of this passive pixel device may be found in co-pending application, Ser. No. 08/976,976, entitled "Reduced Area Imaging Devices Incorporated Within Surgical Instruments," now U.S. Pat. No. 5,986,693, and is hereby incorporated by reference.

In addition to the active pixel-type CMOS imager which is disclosed in U.S. Pat. No. 5,471,515, there have been developments in the industry for other solid state imagers which have resulted in the ability to have a "camera on a chip." For example, Suni Microsystems, Inc. of Mountain View, Calif., has developed a CCD/CMOS hybrid which combines the high quality image processing of CCDs with standard CMOS circuitry construction. In short, Suni Microsystems, Inc. has modified the standard CMOS and CCD manufacturing processes to create a hybrid process providing CCD components with their own substrate which is separate from the P well and N well substrates used by the CMOS components. Accordingly, the CCD and CMOS components of the hybrid may reside on different regions of the same chip or wafer. Additionally, this hybrid is able to run on a low power source (5 volts) which is normally not possible on standard CCD imagers which require 10 to 30 volt power supplies. A brief explanation of this CCD/CMOS hybrid can be found in the article entitled "Startup Suni Bets on Integrated Process" found in *Electronic News,* Jan. 20, 1997 issue. This reference is hereby incorporated by reference for purposes of explaining this particular type of imaging processor.

Another example of a recent development in solid state imaging is the development of a CMOS imaging sensor which is able to achieve analog to digital conversion on each of the pixels within the pixel array. This type of improved CMOS imager includes transistors at every pixel to provide digital instead of analog output that enable the delivery of decoders and sense amplifiers much like standard memory chips. With this new technology, it may, therefore, be possible to manufacture a true digital "camera on a chip." This CMOS imager has been developed by a Stanford University joint project and is headed by Professor Abbas el-Gamal.

A second approach to creating a CMOS-based digital imaging device includes the use of an over-sample converter at each pixel with a one bit comparator placed at the edge of the pixel array instead of performing all of the analog to digital functions on the pixel. This new design technology has been called MOSAD (multiplexed over sample analog to digital) conversion. The result of this new process is low power usage, along with the capability to achieve enhanced dynamic range, possibly up to 20 bits. This process has been developed by Amain Electronics of Simi Valley, Calif. A brief description of both of the processes developed by Stanford University and Amain Electronics can be found in an article entitled "A/D Conversion Revolution for CMOS Sensor?," September 1998 issue of *Advanced Imaging.* This article is also hereby incorporated by reference for purposes of explaining these particular types of imaging processors.

Yet another example of a recent development with respect to solid state imaging is an imaging device developed by ShellCase, of Jerusalem, Israel. In an article entitled "A CSP Optoelectronic Package for Imaging and Light Detection Applications" (A. Badihi), ShellCase introduces a diesized, ultrathin optoelectronic package which is completely packaged at the wafer level using semiconductor processing. In short, ShellCase provides a chip scale package (CSP) process for accepting digital image sensors which may be used, for example, in miniature cameras. The die-sized, ultrathin package is produced through a wafer level process which utilizes optically clear materials and completely encases the imager die. This packaging method, ideally suited for optoelectronic devices, results in superior optical performance and form factor not available by traditional image sensors. This article is also incorporated by reference for purposes of explaining ShellCase's chip scale package process.

Yet another example of a recent development with respect to solid state imaging is shown in U.S. Pat. No. 6,020,581 entitled "Solid State CMOS Imager Using Silicon on Insulator or Bulk Silicon." This patent discloses an image sensor incorporating a plurality of detector cells arranged in an array wherein each detector cell as a MOSFET with a floating body and operable as a lateral bipolar transistor to amplify charge collected by the floating body. This invention overcomes problems of insufficient charge being collected in detector cells formed on silicon on insulator (SOI) substrates due to silicon thickness and will also work in bulk silicon embodiments.

The above-mentioned developments in solid state imaging technology have shown that "camera on a chip" devices will continue to be enhanced not only in terms of the quality of imaging which may be achieved, but also in the specific construction of the devices which may be manufactured by new breakthrough processes.

Although the "camera on a chip" concept is one which has great merit for application in many industrial areas, a need still exists for a reduced area imaging device which can be used in even the smallest type of industrial application. Recently, devices known as palm top computers, PDA(s), or hand-held computers have become very popular items. Essentially, these PDAs are miniature computers, small enough to be held in the hand, which have various software programs available to a user including word processing, e-mail, and organization software for addresses/phone books, etc.

One example of a U.S. patent disclosing a type of a PDA includes U.S. Pat. No. 5,900,875. This patent is incorporated herein by reference for purposes of illustrating an example of a PDA including basic functionality for such a device. In a recent article entitled "Palm, Inc. Gets Ready for New Hands" appearing in the *Wallstreet Journal,* a number of soon to be commercially available PDAs are disclosed. One such device disclosed in this article is known as the "Hand Spring Visor Deluxe." This device will soon be available which allows a user to accommodate pagers, MP3 players, still digital cameras and other devices.

It is one general object of this invention to provide a video system in combination with a standard PDA enabling a user to take video images by a very small camera module incorporated within the PDA, view the video images taken on a video viewscreen incorporated within the PDA, and to have the capability to store, download the video images, and send the video images electronically through a communications network.

Another object of this invention is to provide a PDA with the ability to not only transmit video images taken by the camera module, but also to receive video images sent from a remote location via the communications network, and to view such received video images on the video view screen of the PDA. Accordingly, the invention is ideally suited for video teleconferencing.

It is another object of this invention to provide a reduced area imaging device incorporated within a PDA which takes advantage of "camera on a chip" technology, but to rearrange the video processing circuitry in a selective stacked relationship so that the camera module has a minimum profile.

It is yet another object of this invention to provide imaging capability for a PDA wherein the video camera used is of such small size that it can be stored in the PDA when not in use. The camera module is attached to the PDA by a retractable cord which enables the imaging device to be used to image anything at which the camera module is pointed by the user without having to also move the PDA away from the view of the user.

In all applications, to include use of the imaging device of this invention with a PDA, "camera on a chip" technology can be improved with respect to reducing its profile area, and incorporating such a reduced area imaging device within a PDA such that minimal size and weight is added to the PDA, and further that the imaging device can be used to image selected targets by the user.

DISCLOSURE OF THE INVENTION

In accordance with the present invention, reduced area imaging devices are provided in combination with a hand-held computer or PDA. The term "imaging device" as used herein describes the imaging elements and processing circuitry which is used to produce a video signal which may be accepted by both a standard video device such as a television or video monitor accompanying a personal computer, and a small LCD screen which is incorporated within the PDA. The term "image sensor" as used herein describes the components of a solid state imaging device which captures images and stores them within the structure of each of the pixels in the array of pixels found in the imaging device. As further discussed below, the timing and control circuits can be placed either on the same planar structure as the pixel array, in which case the image sensor can also be defined as an integrated circuit, or the timing and control circuitry can be placed remote from the pixel array. The terms "video signal" or "image signal" as used herein, and unless otherwise more specifically defined, refer to an image which at some point during its processing by the imaging device, is found in the form of electrons which have been placed in a specific format or domain. The term "processing circuitry" as used herein refers to the electronic components within the imaging device which receive the image signal from the image sensor and ultimately place the image signal in a usable format. The terms "timing and control circuits" or "timing and control circuitry" as used herein refer to the electronic components which control the release of the image signal from the pixel array.

In a first arrangement, the image sensor, with or without the timing and control circuitry, may be placed at the distal tip of a very small camera module which is attached by a cable or cord to the PDA, while the remaining processing circuitry may be placed within the housing of the PDA.

In a second arrangement, the image sensor and the processing circuitry may all be placed in a stacked arrangement of miniature circuit boards or planar circuit structures and positioned at the distal tip of the camera module. In this second arrangement, the pixel array of the image sensor may be placed by itself on its own circuit board while the timing and control circuitry and processing circuitry are placed on one or more other circuit boards, or the circuitry for timing and control may be placed with the pixel array on one circuit board, while the remaining processing circuitry can be placed on one or more of the other circuit boards.

In yet another alternative arrangement, the pixel array, timing and control circuits, and some of the processing circuitry can be placed near the distal end of the camera module on two or more circuit boards with the remaining part of the processing circuitry being placed in the housing of the PDA.

For the arrangement or configuration of the imaging device which calls for the array of pixels and the timing and control circuitry to be placed on the same circuit board, only one conductor is required in order to transmit the image signal to the video processing circuitry. When the timing and control circuits are incorporated onto other circuit boards, a plurality of connections are required in order to connect the timing and control circuitry to the pixel array, and then the one conductor is also required to transmit the image signal back to the video processing circuitry.

As mentioned above, the invention disclosed herein can be considered an improvement to a PDA wherein the improvement comprises a video system. The video system would include the video view screen or monitor attached to the PDA, the camera module, as well as supporting video processing circuitry for the imaging device. In yet another aspect, the invention disclosed herein can also be considered an improvement to a PDA wherein the improvement comprises a novel imaging device, preferably of CMOS construction. For this improvement comprising the imaging device, the imaging device includes the array of pixels, and the supporting video processing circuitry for providing a video ready signal.

This video ready signal may be formatted by the video processing circuitry for viewing on a NTSC/PAL compatible device such as television, or for viewing on a VGA compatible device such as a monitor of a personal computer. Of course, the video ready signal is formatted for viewing the video images on the video view screen incorporated within the PDA.

In yet another aspect, the invention disclosed herein can also be considered an improvement to a PDA wherein the improvement comprises a combination of a video system, and wireless telephone communication means for transmitting and receiving both audio and video signals. In this aspect, the invention has functionality for transmitting and receiving audio and video signals via the communications network. One example of a U.S. patent disclosing wireless remote communications between a personal computer and a PDA or miniature hand held computer is U.S. Pat. No. 6,034,621. This patent is hereby incorporated by reference in its entirety for purposes of disclosing means by which data can be exchanged between the hand held computer and a personal computer, to include video and audio signals. The specific example in this patent which readily lends itself to the communication network incorporated within this invention is found at FIG. 4 of this '621 patent. The discussion further below outlines this particular communication network.

In yet another aspect, the invention disclosed herein can also be considered an improvement to a PDA wherein the improvement comprises a video system, and a standard wireless telephone communication means for transmitting and receiving audio signals. In this aspect, the PDA simply includes a standard wireless/cellular phone connected externally on the PDA which enables the user to conduct well-known wireless/telephone communications. This wireless/cellular communication means can be in addition to the wireless telephone communication means for transmitting and receiving both audio and video signals discussed immediately above with respect to the U.S. Pat. No. 6,034,621.

Another example of a U.S. patent disclosing basic mobile phone technology including a discussion of basic phone circuitry is U.S. Pat. No. 6,018,670. This patent is hereby incorporated by reference in its entirety for purposes of disclosing standard or basic mobile phone technology and supporting circuitry.

Accordingly, the invention disclosed herein has utility with respect to an overall combination of elements, as well as various sub-combination of elements.

BRIEF DESCRIPTION OF THE DRAWINGS

FIG. 1 is an enlarged fragmentary partially exploded perspective view of the distal end of the camera module which is used in conjunction with the PDA, specifically illustrating the arrangement of the image sensor with respect to the other elements of the camera module;

FIG. 1a is an enlarged exploded perspective view illustrating another configuration of the image sensor wherein video processing circuitry is placed behind and in longitudinal alignment with the image sensor;

FIG. 2 is a perspective view of the PDA incorporating the reduced area imaging device of this invention;

FIG. 3 illustrates the PDA of FIG. 2 wherein the camera module is in the retracted position;

FIG. 5 is a schematic diagram illustrating an example communications network which can be used for data transfer of text, audio, and visual signals between the PDA and a personal computer which is in communication with the world wide web;

FIG. 6a is a perspective view of the PDA in combination with an externally attached wireless/cellular phone;

FIG. 6b is another perspective view of the combination of FIG. 6a illustrating the combination opened to expose the PDA;

FIG. 7 is a more detailed schematic diagram of the functional electronic components which make up the imaging device;

BEST MODE FOR CARRYING OUT THE INVENTION

Figure 4:
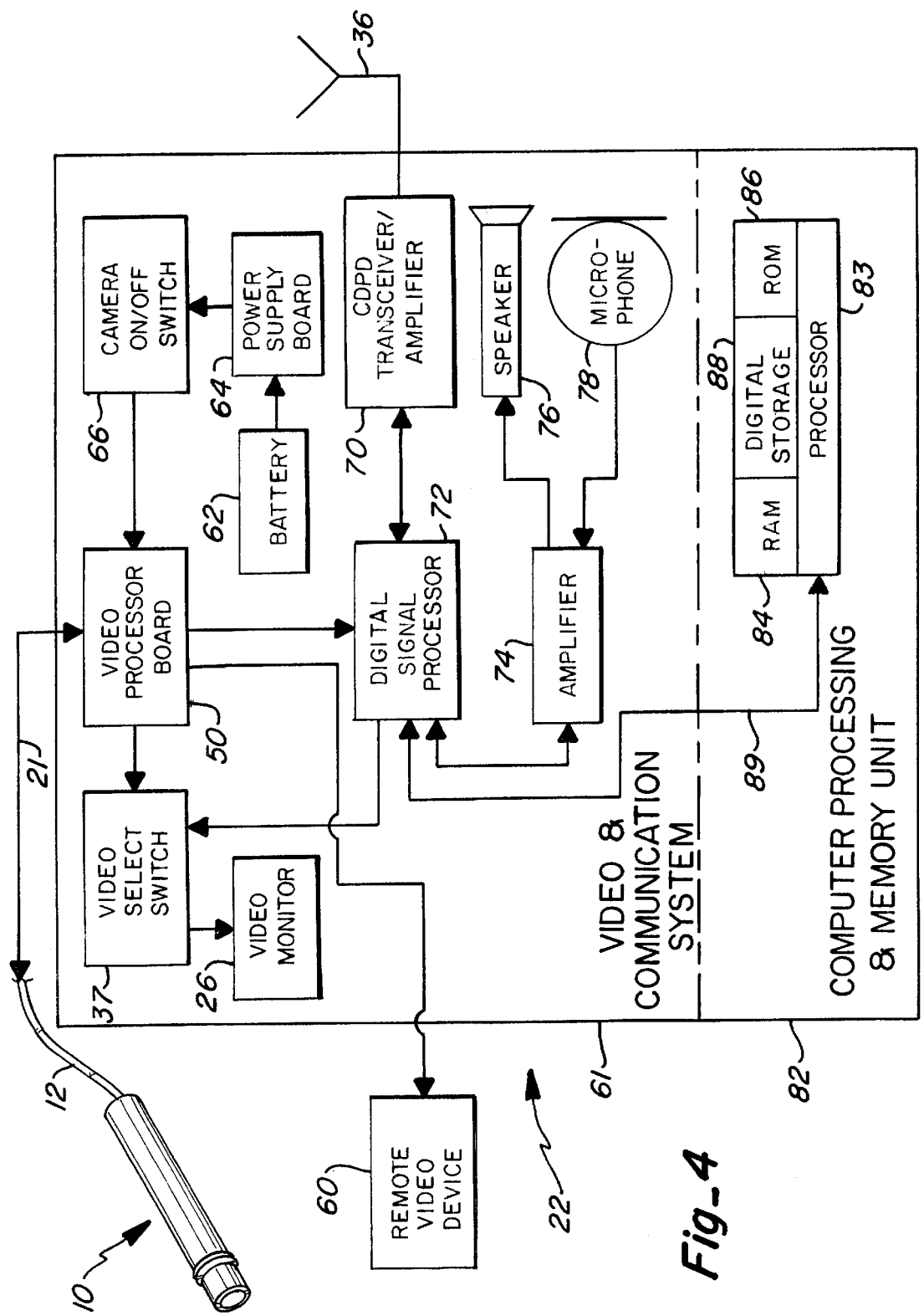
FIG. 4 is an overall schematic diagram of the functional electronic components which make up both the PDA and the reduced area imaging device wherein communications are achieved by wireless/cellular technology for video teleconferencing via the world wide web which is well-known as a global communications network.

In accordance with the invention, as shown in FIG. 1, a camera module 10 is provided which incorporates a reduced area imaging device 11. As further discussed below, the elements of the imaging device 11 may all be found near one location, or the elements may be separated from one another and interconnected by the appropriate wired connections. The array of pixels making up the image sensor captures images and stores them in the form of electrical energy by conversion of light photons to electrons. This conversion takes place by the photo diodes in each pixel which communicate with one or more capacitors which store the electrons. Specifically, the camera module 10 includes an outer tube/sheath 14 which houses the components of the imaging device. The camera module is shown as being cylindrical in shape having a window 16 sealed at the distal end of the camera module. A retractable cable 12 extends from the proximal end of the camera module 10. A shielded cable 21 is used to house the conductors which communicate with the imaging device 11. The shielded cable 21 is then housed within the retractable cable 12. A lens group 18 is positioned at the distal end of the camera module to enable an image to be appropriately conditioned prior to the image impinging upon the imaging device 11. Also shown is a focusing ring 20 which enables the lens group 18 to be displaced distally or proximally to best focus an image on the imaging device 11.

Now referring to FIGS. 2 and 3, a PDA 22 is shown which incorporates the camera module 10. In basic terms, the PDA 22 is a miniature hand-held computer incorporating a video system enabling video to be taken by the camera module, and viewed on the video view screen 26, as well as enabling images to be stored and downloaded on a miniature computer disc (not shown) used with the PDA. Also discussed further below is the ability to transmit and receive audio and video signals.

Beginning first with a description of the basic components of the PDA 22, it includes a housing 24 which hold the components of the PDA and the video system. Cable 12 is housed within the housing 24 when in the retracted position. A spring biased spool (not shown) or some other known retracting device is mounted within the housing 24 enabling the cable 12 to be extended or retracted. A plurality of controls are provided enabling the user to manipulate the functions of the PDA. These are shown as buttons 34 on the housing 24. The video view screen 26 is used for displaying video images taken by the camera module 10, or for viewing incoming video signals received from a remote location. A command screen 28 is provided which allows a user to select programs with a stylus (not shown). A video capture button 30 is provided which allows a user to capture a still video image taken by the camera module 10. A video store button 32 is also provided which enables a captured video image to be stored within the digital memory of the PDA, as further discussed below. An opening or cavity 35 is provided which allows the camera module 10 to be stored, along with cable 12 within the housing 24. As shown in FIG. 3, the camera module 10 is in the stored or retracted position. The antenna 36 allows for enhanced transmission and reception of incoming or transmitted/outgoing audio and video signals. A video select switch 37 is provided enabling a user to view either video images taken by the camera module 10, or for viewing incoming video images. The video view screen 26 may be a liquid crystal display (LCD) type, or any other well-known display device of high resolution which has low power requirements, and has minimum size requirements as well.

An example of a manufacture of such a miniature LCD monitor includes DISPLAYTECH of Longmont, Colo. DISPLAYTECH manufactures a miniature reflective display that consists of ferroelectric liquid crystal (FLC) applied to a CMOS integrated circuit. The reflective display is a VGA display panel having low voltage digital operation, low power requirements, and full color operation. One of their specific products includes the LightCaster™ VGA Display Panel, Model LDP-0307-MV1. This is but one example of an LCD monitor which is available and usable within the invention herein described.

A camera on/off switch 66 is provided enabling the user to turn the video system on or off. Also shown in FIGS. 2 and 3 is a speaker 76 and a microphone 78 which are used for sending and receiving audio signals in the conventional manner as with a wireless/cellular telephone. A further description of speaker 76 and microphone 78 is found below.

Referring back to FIGS. 1 and 1a, the imaging device 11 includes an image sensor 40. FIG. 1 illustrates that the image sensor 40 can be a planar and square shaped member, or alternatively, planar and circular shaped to better fit within outer tube 14. In the configuration of the imaging device in FIGS. 1 and 1a, there are only three conductors which are necessary for providing power to the image sensor 40, and for transmitting an image from the image sensor 40 back to the processing circuitry found within the phone housing 24. Specifically, there is a power conductor 44, a grounding conductor 46, and an image signal conductor 48, each of which are hardwired to the image sensor 40. Thus, shielded cable 21 may simply be a three conductor, 50 ohm type cable.

Image sensor 40 can be as small as 1 mm in its largest dimension. However, a more preferable size for most PDA applications would be between 4 mm to 8 mm in the image sensor's largest dimension (height or width). The image signal transmitted from the image sensor 40 through conductor 48 is also herein referred to as a pre-video signal. Once the pre-video signal has been transmitted from image sensor 40 by means of conductor 48, it is received by video processing board 50, as shown in FIG. 7. Video processing board 50 then carries out all the necessary conditioning of the pre-video signal and places it in a form, also referred to herein as a video ready signal, so that it may be viewed directly on a remote video device such as a television or standard computer video monitor. In order for the pre-video signal to be viewed on the video view screen/monitor 26, the pre-video signal is further conditioned by a digital signal processor 72, as further discussed below. The video signal produced by the video processing board 50 can be viewed by an NTSC/PAL compatible video device (such as a television) which connects to the PDA through a remote jack. This video signal produced by board 50 can be further defined as a post-video signal.

FIG. 1 illustrates an arrangement wherein the image sensor 40 is placed by itself adjacent the distal end of the camera module 10. Alternatively, some or all of the video processing circuitry may be placed in adjacent circuit boards directly behind the image sensor 40. Accordingly, 1a illustrates video processor board 50 aligned directly behind the image sensor 40. A plurality of pin connectors 52 can be used to interconnect image sensor 40 to video processor board 50. Depending upon the specific configuration of image sensor 40, pin connectors 52 may be provided for structural support only, and/or to provide a means by which image signals are transmitted between image sensor 40 and board 50. Additionally, digital signal processor 72 could also be placed behind image sensor 40 and behind video processing board 50. Accordingly, the image sensor, and all supporting video processing circuitry could be placed at the distal end of the camera module 10. However, because of the ample space within housing 24, it may be preferable to place at least some of the video processing circuitry within housing 24. In the case of FIG. 1a, the conductor 49 represents the conductor which may carry the post-video signal for direct connection with a remote video device 60 such as a television or computer monitor. As also discussed further below, placement of the digital signal processor 72 at the distal tip of the camera module behind the video processing board 50 would also enable yet another conductor (not shown) to connect directly to the video monitor 26 for transmitting a video signal to the video monitor 26.

Again referring to FIGS. 1 and 1a, the area which is occupied by image sensor 40 may be defined as the profile area of the imaging device and which determines its critical dimensions. If it is desired to place video processing circuitry adjacent the image sensor 40 at the distal end of the camera module 10, such circuitry must be able to be placed on one or more circuit boards which are longitudinally aligned with image sensor 40 along longitudinal axis XX. If it is not important to limit the size of the profile area, then any circuitry placed behind image sensor 40 can be aligned in an offset manner, or may simply be larger than the profile area of image sensor 40. In the configuration shown in FIG. 1a, it is desirable that elements 40 and 50 be approximately the same size so that they may uniformly fit within the distal end of outer tube 14.

Now referring to FIG. 4, a further explanation is provided of the basic electronic components of the PDA 22. The PDA 22 of this invention includes functionality normally found in multiple devices. Specifically, the PDA 22 includes the computing capability of a PDA, a mobile/wireless phone, communication means for connection to a computer network such as the worldwide web, and a video system. The PDA 22 may be separated into two major groups, namely, a video and communication system 61, and a computer processing and memory unit 82. Both of these are discussed in further detail below.

As shown in FIG. 4, a conventional lithium ion battery 62 is provided which communicates with power supply board 64. Power supply board 64 conditions various power outputs to the components of the device, to include power to the video components. In the preferred imaging device of this invention, the power to the imaging device may simply be direct current of between about 1.5 to 12 volts, depending upon the power requirements of the imaging device. A camera on/off switch 66 must be set to the "on" position in order to activate the camera module 10. The video processor board 50 then transfers power to supplies the camera module 10, and also receives the analog pre-video signal back from the camera module, as further discussed below. After processing of the pre-video signal at the video processor board 50, the video signal is video ready, meaning that it may then be directly viewed on a remote compatible video device 60, such as a television or computer monitor. A video port 54 can be provided on the housing 24 enabling a user to take a standard video jack (not shown) and interconnect the PDA with the video port of the remote video device. The video format for such remote video devices includes NTSC/PAL and VGA; thus, the video signal processed by video processor board 50 creates the video ready signals for use with these remote video devices. For purposes of viewing images on the monitor 26, the pre-video signal is further processed into a digital format within video processor board 50, preferably an 8 bit component video signal format that is commonly referred to as "YUV 4:2:2." This video format easily lends itself to video compression. This 8 bit digital video signal is then sent to the digital signal processor 72 which performs two functions relevant to the video signal. The digital signal processor 72 further converts the signal into a format that is compatible with the driver circuitry of the video monitor 26. Secondly, the digital signal processor 72 compresses the YV signal using a common video compression format, preferably JPEG. The JPEG encoded video signal is then mixed with the audio signal created by microphone 78 and amplifier 74, and the resulting high frequency carrier signal may then be passed onto the transceiver/amplifier section 70 for transmission. It is to be understood that the transceiver/amplifier 70 is intended for communication with well-known wide area wireless communication networks. It is also contemplated within the spirit and scope of this invention that the PDA 22 be capable of communication with computer networks to include the worldwide web. Accordingly, the invention is well adapted for conducting video teleconferencing which is normally conducted with desktop computers and supplemental video equipment. The transceiver/amplifier section also modulates the carrier signal prior to transmission. Depending upon the position of video switch 37, the video signal from digital signal processor 72 is either sent to the monitor 26, or is sent to the transceiver/amplifier section 70 for transmission. As also shown, the antenna 36 is used for enhancement of reception and transmission of transmitted and received carrier signals.

The transceiver/amplifier section 70 also serves as a receiver which receives an incoming carrier signal. This incoming signal is then demodulated within section 70, the video and audio components of the incoming signal are separated, and then these separated signals are then sent to the digital signal processor 72 which performs video decompression. Then, the decompressed video signal is sent to the monitor 26 for viewing (if the video switch 37 is placed in that selected mode). The decompressed audio signal is sent to the amplifier 74, and then to the speaker 76.

FIG. 4 shows the transceiver/amplifier section 70 as being a cellular digital packet data system (CDPD) type transceiver. This particular transceiver/amplifier 70 could be the same as that disclosed in the U.S. Pat. No. 6,034,621. A cellular digital packet system is a wireless standard providing two-way, 19.2 kbps packet data transmission over existing cellular telephone channels.

The video switch 37 may simply be a momentary, spring loaded, push button-type switch. When the video switch 37 is not depressed, incoming video, which is received via the antenna 36, is processed as discussed above in the transceiver/amplifier section 70 and digital signal processor 72, and then sent to the monitor 26. When the video switch 37 is depressed and held, the video signal produced from the camera module 10 is processed as discussed above, and ultimately sent to the monitor 26 for viewing by the user. An operator can cycle the switch 37 between the two positions in order to selectively choose whether to view incoming or outgoing video.

FIG. 5 illustrates a communications network which can be used by the invention. A communications network of this type is disclosed in the U.S. Pat. No. 6,034,621, and is discussed specifically therein at FIGS. 3 and 4 of that patent. FIG. 5 illustrates a CDPD base station 182 with a remote computer 188 utilizing a direct connection to the CDPD base station 182 via a modem 186 with a dial-up connection to the public switch telephone network (PSTN) 184. The CDPD base station 182 includes an antenna 181. The remote computer 188 can be a personal computer, a server, or any other well-known stand-alone computer.

Referring back to FIG. 4, the computer processing and memory unit 82 which allows the PDA 22 to achieve basic word processing, etc., includes a microprocessor 83, RAM 84, ROM 86, and digital storage 88. Digital storage 88 is provided for storing the formatted images taken by the camera module 10. The RAM 84, microprocessor 83, and ROM 86 are conventional or standard components as found in existing PDAs. An input/output bus 89 is provided which allows video signals to be stored or otherwise manipulated within the computer processing and memory unit 82. Accordingly, video taken by camera module 10 can be downloaded to digital storage 88. Also, existing image data stored in digital storage 88 could be viewed on video monitor 26.

FIGS. 6a and 6b illustrate another combination of the invention wherein the PDA 22 is simply combined with an externally mounted cellular telephone 190. The cellular phone 190 is a commercially available cellular/wireless telephone. As shown, the telephone includes the standard keypad 194, visual display 196, and antennae 198. The phone 190 is secured to the PDA 22 as by mounting means 192, which is shown in the preferred embodiment as a piano-type hinge. Thus, the PDA is altered very simply by providing means by which a cellular telephone can be attached to the PDA. This enables the user to hold both the PDA and cellular telephone in one hand while manipulating the PDA or phone 190 as desired with the other hand. All of the telephone circuitry for phone 190 is housed within the phone itself, and there is no circuitry within the PDA which is used within the phone 190.

The actual size of the phone 190 is smaller than the PDA 22. However, in order to create a uniform edged combination, the phone 190 is housed in a larger housing 200 which essentially matches the dimensions of housing 24. Additionally, a peripheral flange could be provided on the inner surface of housing 200 which comes into contact with housing 24 in the closed position of FIG. 6a which would prevent inadvertent activation of the control buttons on the PDA 22.

FIG. 7 is a schematic diagram illustrating one way in which the imaging device 11 may be constructed. As illustrated, the image sensor 40 may include the timing and control circuits on the same planar structure. Power is supplied to image sensor 40 by power supply board 64. The connection between image sensor 40 and board 64 may simply be a cable having two conductors therein, one for ground and another for transmitting the desired voltage. These are illustrated as conductors 44 and 46. The output from image sensor 40 in the form of the pre-video signal is input to video processor board 50 by means of the conductor 48. In the configuration of FIG. 7, conductor 48 may simply be a 50 ohm conductor. Power and ground also are supplied to video processing board 50 by conductors 44 and 46 from power supply board 52. The output signal from the video processor board 50 is in the form of the post-video signal and which may be carried by conductor 49 which can also be a 50 ohm conductor.

Although FIG. 7 illustrates the image sensor and the timing and control circuits being placed on the same circuit board or planar structure, it is possible to separate the timing and control circuits from the pixel array and place the timing and control circuits onto video processing board 50. The advantage in placing the timing and control circuits on the same planar structure as the image sensor is that only three connections are required between image sensor 40 and the rest of the imaging device, namely, conductors 44, 46 and 48. Additionally, placing the timing and control circuits on the same planar structure with the pixel array results in the pre-video signal having less noise. Furthermore, the addition of the timing and control circuits to the same planar structure carrying the image sensor only adds a negligible amount of size to one dimension of the planar structure. If the pixel array is to be the only element on the planar structure, then additional connections must be made between the planar structure and the video processing board 50 in order to transmit the clock signals and other control signals to the pixel array. For example, a ribbon-type cable (not shown) or a plurality of 50 ohm coaxial cables (not shown) must be used in order to control the downloading of information from the pixel array. Each of these additional connections would be hard wired between the boards.

Figure 7A:
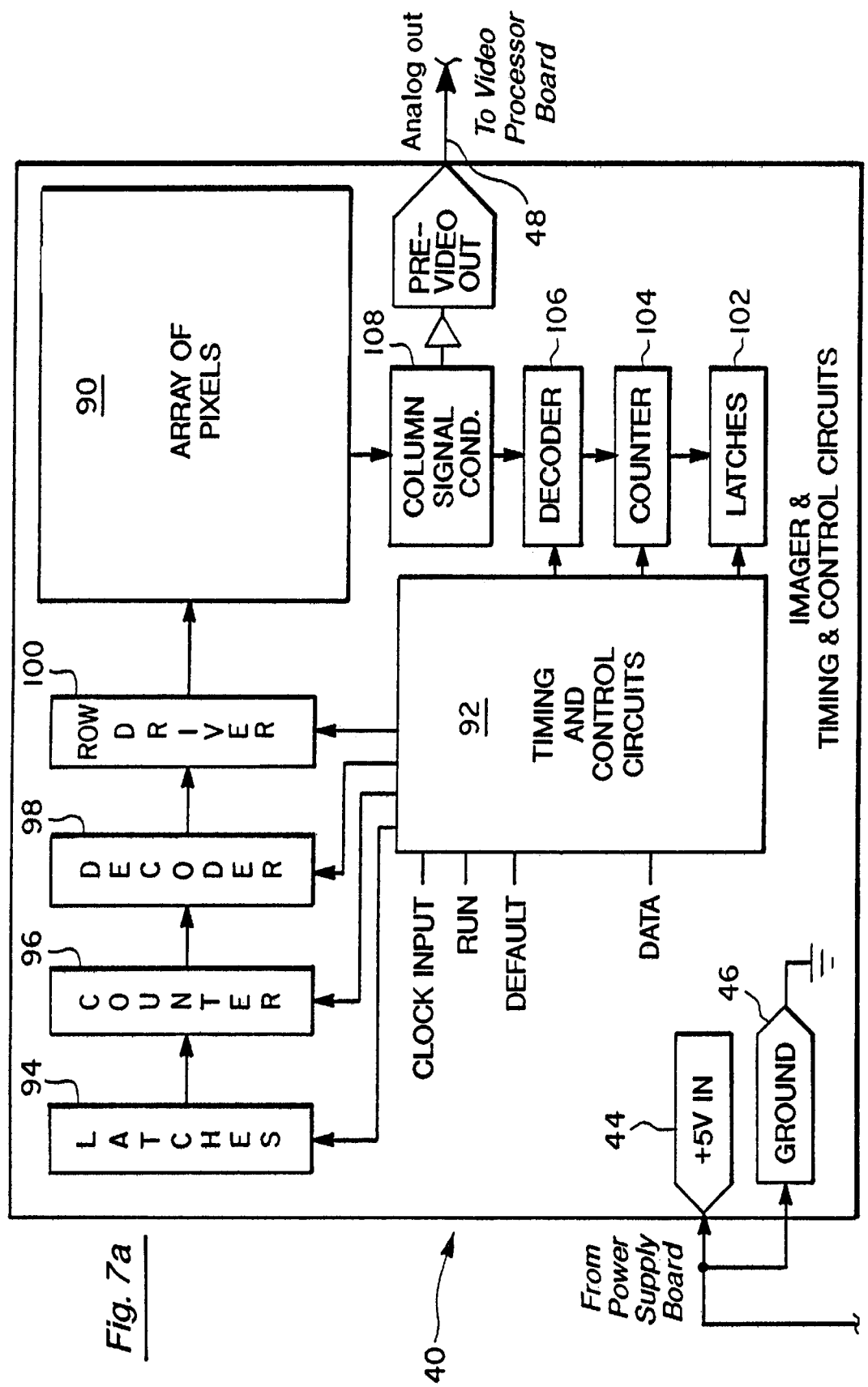
FIG. 7a is an enlarged schematic diagram of a circuit board/planar structure which may include the array of pixels and the timing and control circuitry.
Figure 7B:
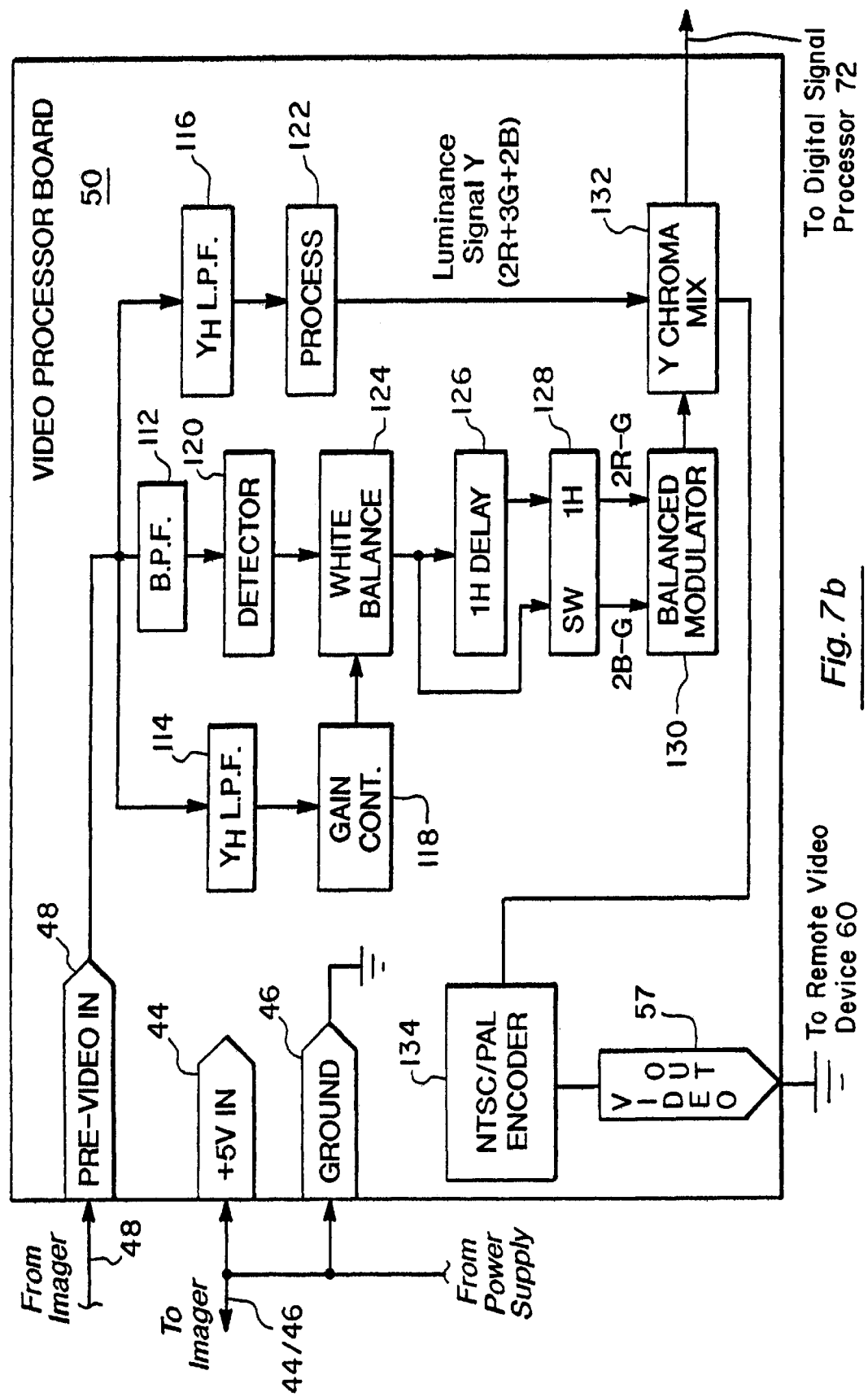
FIG. 7b is an enlarged schematic diagram of a video processing board/planar structure having placed thereon the processing circuitry which processes the pre-video signal generated by the array of pixels and which converts the pre-video signal to a post-video signal which may be accepted by an NTSC/PAL compatible video device.

FIG. 7a is a more detailed schematic diagram of image sensor 40 which contains an array of pixels 90 and the timing and control circuits 92. One example of a pixel array 90 which can be used within the invention is similar to that which is disclosed in U.S. Pat. No. 5,471,515 to Fossum, et al., said patent being incorporated by reference herein. More specifically, FIG. 3 of Fossum, et al. illustrates the circuitry which makes up each pixel in the array of pixels 90. The array of pixels 90 as described in Fossum, et al. is an active pixel group with intra-pixel charged transfer. The image sensor made by the array of pixels is formed as a monolithic complementary metal oxide semiconductor (CMOS) integrated circuit which may be manufactured in an industry standard complementary metal oxide semiconductor process. The integrated circuit includes a focal plane array of pixel cells, each one of the cells including a photo gate overlying the substrate for accumulating the photo generated charges. In broader terms, as well understood by those skilled in the art, an image impinges upon the array of pixels, the image being in the form of photons which strike the photo diodes in the array of pixels. The photo diodes or photo detectors convert the photons into electrical energy or electrons which are stored in capacitors found in each pixel circuit. Each pixel circuit has its own amplifier which is controlled by the timing and control circuitry discussed below. The information or electrons stored in the capacitors is unloaded in the desired sequence and at a desired frequency, and then sent to the video processing board 50 for further processing.

Although the active pixel array disclosed in U.S. Pat. No. 5,471,515 is mentioned herein, it will be understood that the hybrid CCD/CMOS described above, or any other solid state imaging device may be used wherein timing and control circuits can be placed either on the same circuit board or planar structure with the pixel array, or may be separated and placed remotely. Furthermore, it will be clearly understood that the invention claimed herein is not specifically limited to an image sensor as disclosed in the U.S. Pat. No. 5,471,515, but encompasses any image sensor which may be configured for use in conjunction with the other processing circuitry which makes up the imaging device of this invention.

To summarize the different options available in terms of arrangement of the components of the imaging device 11, the array of pixels 90 of the image sensor 40 may be placed alone on a first plane, or the timing and control circuitry 92 may be placed with the array of pixels 90 on the first plane. If the timing and control circuitry 92 is not placed with the array of pixels 90 on the first plane, the timing and control circuitry 92 may be placed by itself on a second plane, or the timing and control circuitry 92 may be placed on a second plane with some or all of the processing circuitry from video processing board 50. The video processing board 50 itself may be placed on one or more planes on corresponding circuit boards containing video processing circuitry. FIG. 1a illustrates a single video processor board 50 located directly behind image sensor 40; however, it shall be understood that additional circuit boards containing additional circuitry may be placed behind the image sensor 40 and behind the video processing board 50. Some or all of the video processing circuitry may be placed within the camera module 10 near the distal end thereof adjacent the image sensor 40. Video processing circuitry which is not placed within the distal end of the camera module 10 may be placed within the housing 24 of the PDA. If video processing circuitry is placed near the distal end of the camera module 10, it is preferable to arrange the video processing circuitry in a stacked relationship behind the image sensor 40. Additionally, it is preferable to place the processing circuitry in a parallel arrangement with respect to image sensor 40 and to center such video processing circuitry along axis X—X in order to minimize the size of camera module 10.

The timing and control circuits 92 are used to control the release of the image information or image signal stored in the pixel array. In the image sensor of Fossum, et al., the pixels are arranged in a plurality of rows and columns. The image information from each of the pixels is first consolidated in a row by row fashion, and is then downloaded from one or more columns which contain the consolidated information from the rows. As shown in FIG. 7a, the control of information consolidated from the rows is achieved by latches 94, counter 96, and decoder 98. The operation of the latches, counter and decoder is similar to the operation of similar control circuitry found in other imaging devices. That is, a latch is a means of controlling the flow of electrons from each individual addressed pixel in the array of pixels. When a latch 94 is enabled, it will allow the transfer of electrons to the decoder 98. The counter 96 is programmed to count a discrete amount of information based upon a clock input from the timing and control circuits 92. When the counter 96 has reached its set point or overflows, the image information is allowed to pass through the latches 94 and be sent to the decoder 98 which places the consolidated information in a serial format. Once the decoder 98 has decoded the information and placed it in the serial format, then the row driver 100 accounts for the serial information from each row and enables each row to be downloaded by the column or columns. In short, the latches 94 will initially allow the information stored in each pixel to be accessed. The counter 96 then controls the amount of information flow based upon a desired time sequence. Once the counter has reached its set point, the decoder 98 then knows to take the information and place it in the serial format. The whole process is repeated, based upon the timing sequence that is programmed. When the row driver 100 has accounted for each of the rows, the row driver reads out each of the rows at the desired video rate.

The information released from the column or columns is also controlled by a series of latches 102, a counter 104 and a decoder 106. As with the information from the rows, the column information is also placed in a serial format which may then be sent to the video processing board 50. This serial format of column information is the pre-video signal carried by conductor 48. The column signal conditioner 108 places the column serial information in a manageable format in the form of desired voltage levels. In other words, the column signal conditioner 108 only accepts desired voltages from the downloaded column(s).

The clock input to the timing and control circuits 92 may simply be a quartz crystal timer. This clock input is divided into many other frequencies for use by the various counters. The run input to the timing and control circuit 92 may simply be an on/off control. The default input can allow one to input the pre-video signal to a video processor board which may run at a frequency of other than 30 hertz. The data input controls functions such as zoom. At least for a CMOS type active pixel array which can be accessed in a random manner, features such as zoom are easily manipulated by addressing only those pixels which locate a desired area of interest by the user.

A further discussion of the timing and control circuitry which may be used in conjunction with an active pixel array is disclosed in U.S. Pat. No. 5,471,515 and is also described in an article entitled "Active Pixel Image Sensor Integrated With Readout Circuits" appearing in *NASA Tech Briefs*, October 1996, pp. 38 and 39. This particular article is also incorporated by reference.

Once image sensor 40 has created the pre-video signal, it is sent to the video processing board 50 for further processing. At board 50, as shown in FIG. 6b, the pre-video signal is passed through a series of filters. One common filter arrangement may include two low pass filters 114 and 116, and a band pass filter 112. The band pass filter only passes low frequency components of the signal. Once these low frequency components pass, they are then sent to detector 120 and white balance circuit 124, the white balance circuit distinguishing between the colors of red and blue. The white balance circuit helps the imaging device set its normal, which is white. The portion of the signal passing through low pass filter 114 then travels through gain control 118 which reduces the magnitude or amplitude of this portion to a manageable level. The output from gain control 118 is then fed back to the white balance circuit 124. The portion of the signal traveling through filter 116 is placed through the processor 122. In the processor 122, the portion of the signal carrying the luminance or non-chroma is separated and sent to the Y chroma mixer 132. Any chroma portion of the signal is held in processor 122.

Referring to the output of the white balance circuit 124, this chroma portion of the signal is sent to a delay line 126 where the signal is then further reduced by switch 128. The output of switch 128 is sent through a balanced modulator 130 and also to the Y chroma mixer 132 where the processed chroma portion of the signal is mixed with the processed non-chroma portion. Finally, the output from the Y chroma mixer 132 is sent to the NTSC/PAL encoder 134, commonly known in the art as a "composite" encoder. The composite frequencies are added to the signal leaving the Y chroma mixer 132 in encoder 134 to produce the post-video signal which may be accepted by a television. Additionally, the signal from Y chroma mixer 132 is sent to the digital signal processor 72 so that images can be viewed on monitor 26.

In addition to the functions described above that are achieved by the digital signal processor 72, the processor 72 can also provide additional digital enhancements. Specifically, digital enhancement can sharpen or otherwise clarify the edges of an image viewed on a video screen which might normally be somewhat distorted. Additionally, selected background or foreground images may be removed thus only leaving the desired group of images.

In addition to digital enhancement, the digital signal processor 72 can include other circuitry which may further condition the signal received from board 50 so that it may be viewed in a desired format other than NTSC/PAL. One common encoder which can be used would be an RGB encoder. An RGB encoder separates the signal into the three primary colors (red, green and blue). A SVHS encoder (super video home system) encoder could also be added to processor 72. This type of encoder splits or separates the luminance portion of the signal and the chroma portion of the signal. Some observers believe that a more clear signal is input to the video device by such a separation, which in turn results in a more clear video image viewed on the video device. Another example of an encoder which could be added to processor 72 includes a VGA compatible encoder, which enables the video signal to be viewed on a standard VGA monitor which is common to many computer monitors.

One difference between the arrangement of image sensor 40 and the outputs found in FIG. 3 of the Fossum, et al. patent is that in lieu of providing two analog outputs [namely, VS out (signal) and VR out (reset)], the reset function takes place in the timing and control circuitry 92. Accordingly, the pre-video signal only requires one conductor 48.

FIGS. 8a–8e illustrate in more detail one example of circuitry which may be used in the video processing board 50 in order to produce a post-video signal which may be directly accepted by a NTSC/PAL compatible video device such as a television. The circuitry disclosed in FIGS. 8a–8e is very similar to circuitry which is found in a miniature quarter-inch Panasonic camera, Model KS-162. It will be understood by those skilled in the art that the particular arrangement of elements found in FIGS. 8a–8e are only exemplary of the type of video processing circuitry which may be incorporated in order to take the pre-video signal and condition it to be received by a desired video device.

Figure 8A:
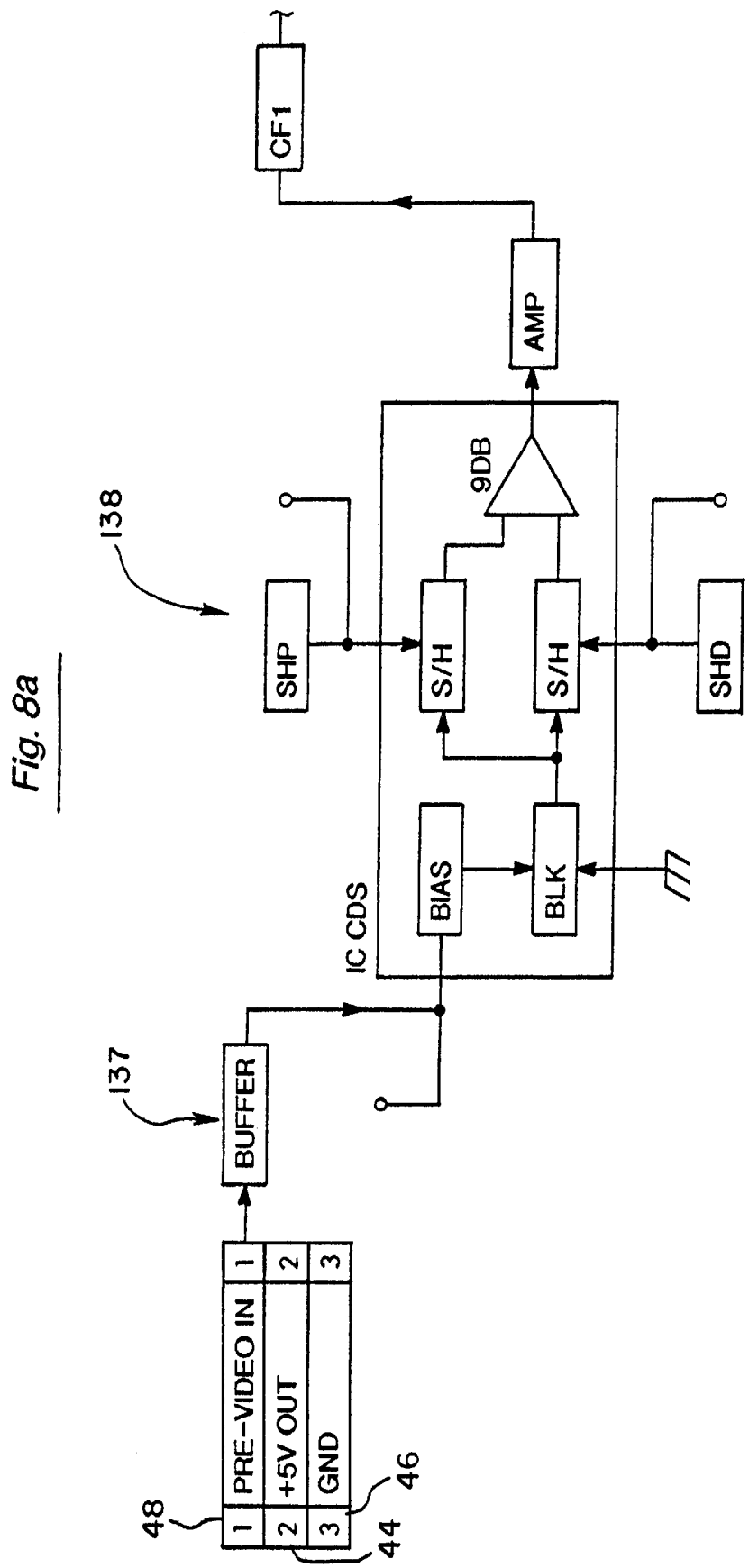
FIGS. 8a–8e are schematic diagrams that illustrate an example of specific circuitry which may be used to make the video processing circuitry of the imaging device.

As shown in FIG. 8a, 5 volt power is provided along with a ground by conductors 44 and 46 to board 50. The pre-video signal carried by conductor 48 is buffered at buffer 137 and then is transferred to amplifying group 138. Amplifying group 138 amplifies the signal to a usable level as well as achieving impedance matching for the remaining circuitry.

Figure 8B:
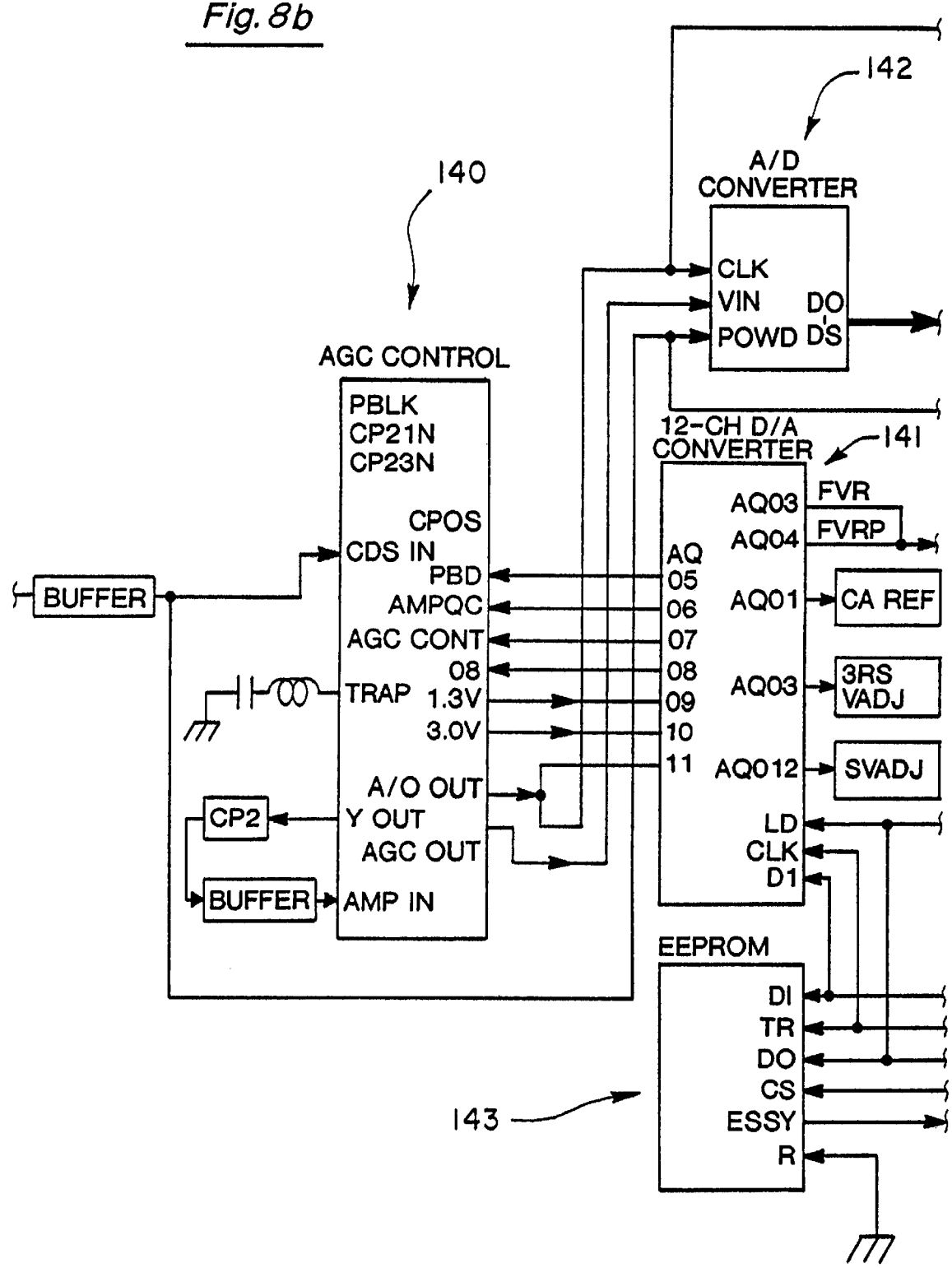

The next major element is the automatic gain control 140 shown in FIG. 8b. Automatic gain control 140 automatically controls the signal from amplifying group 138 to an acceptable level and also adds other characteristics to the signal as discussed below. More specifically, automatic gain control 140 conditions the signal based upon inputs from a 12 channel digital to analog converter 141. Converter 141 retrieves stored information from EEPROM (electrically erasable programmable read only memory) 143. EEPROM 143 is a non-volatile memory element which may store user information, for example, settings for color, tint, balance and the like. Thus, automatic gain control 140 changes the texture or visual characteristics based upon user inputs. Housing 24 could also include buttons for controlling the image viewed on monitor 26 such as a gain control 140. The signal leaving the automatic gain control 140 is an analog signal until being converted by analog to digital converter 142.

Figure 8C:
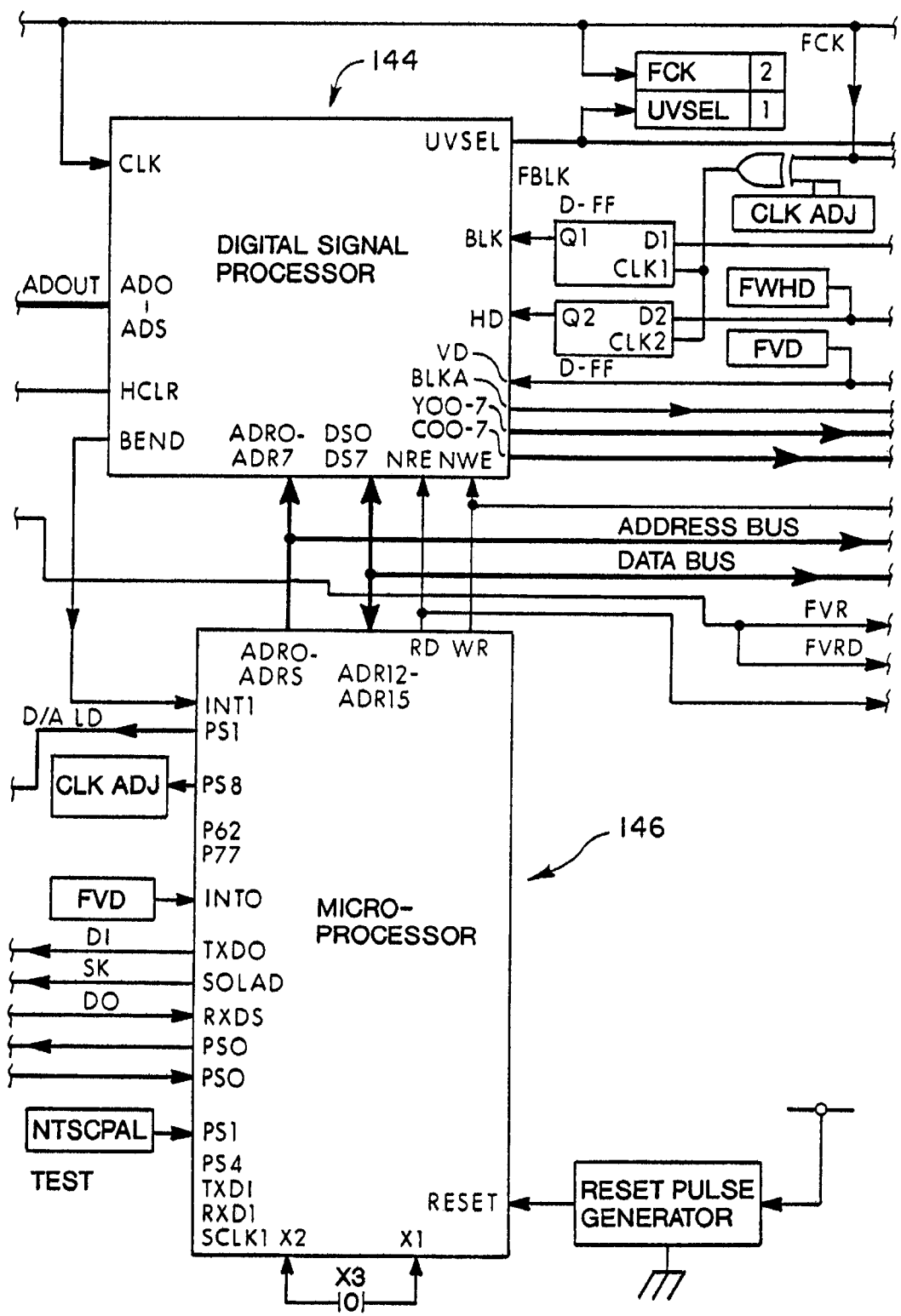

Digital signal processor 144 of FIG. 8c further processes the converted signal into a serial type digital signal. One function of the microprocessor 146 is to control the manner in which digital signal processor 144 sorts the digital signals emanating from converter 142. Microprocessor 146 also controls analog to digital converter 142 in terms of when it is activated, when it accepts data, when to release data, and the rate at which data should be released. Microprocessor 146 may also control other functions of the imaging device such as white balance. The microprocessor 146 may selectively receive the information stored in the EEPROM 143 and carry out its various commands to further control the other elements within the circuitry.

Figure 8D:
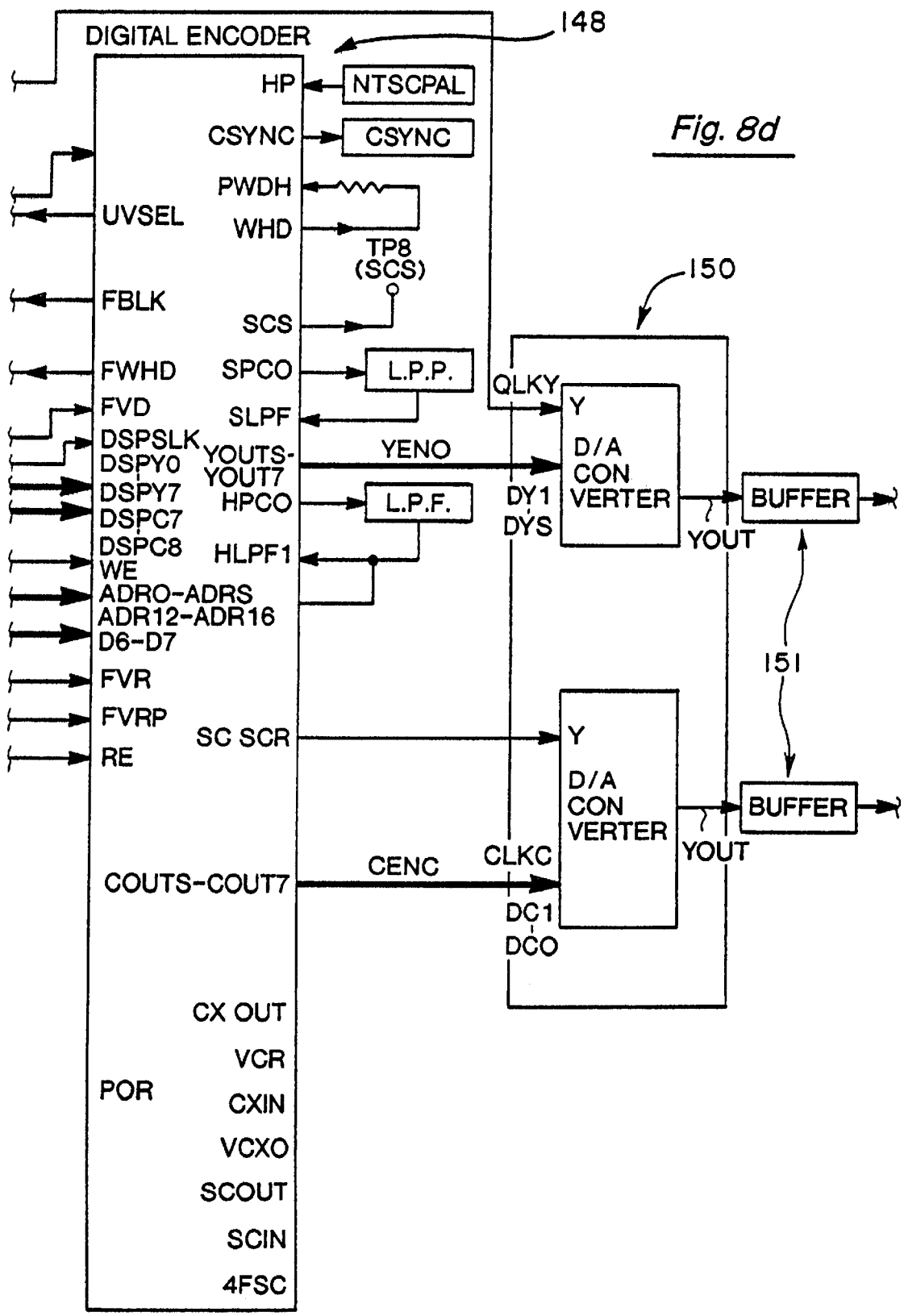

After the signal is processed by digital signal processor 144, the signal is sent to digital encoder 148 illustrated in FIG. 8d. Some of the more important functions of digital encoder 148 are to encode the digital signal with synchronization, modulated chroma, blanking, horizontal drive, and the other components necessary so that the signal may be placed in a condition for reception by a video device such as a television monitor. As also illustrated in FIG. 8d, once the signal has passed through digital encoder 148, the signal is reconverted into an analog signal through digital to analog converter 150.

Figure 8E:
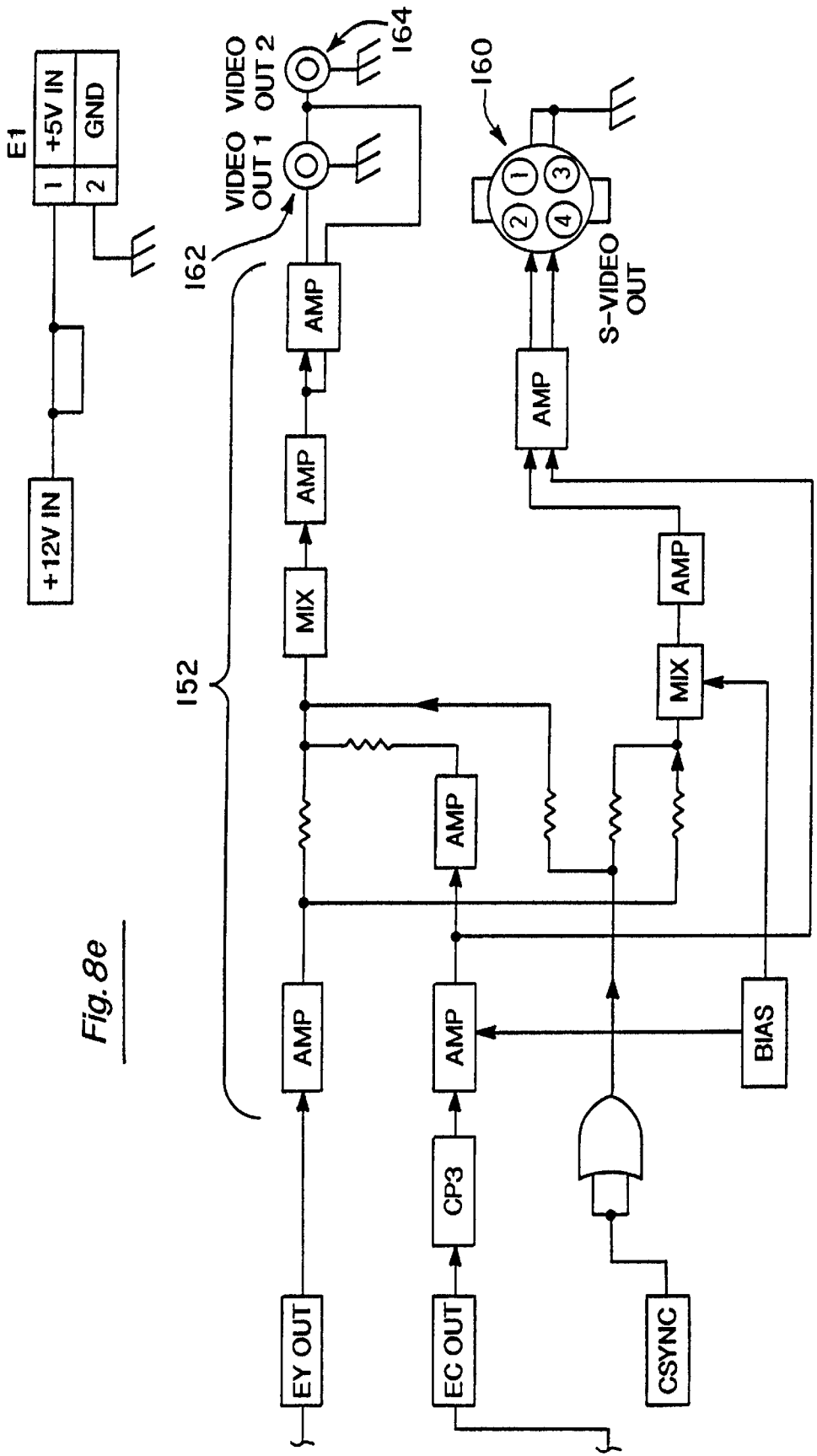

This reconverted analog signal is then buffered at buffers 151 and then sent to amplifier group 152 of FIG. 8e which amplifies the signal so that it is readily accepted by a desired video device. Specifically, as shown in FIG. 8e, one SVHS outlet is provided at 160, and two composite or NTSC outlets are provided at 162 and 164, respectively.

From the foregoing, it is apparent that an entire imaging device may be incorporated within the distal tip of the camera module, or may have some elements of the imaging device being placed in the housing of the PDA. Based upon the type of image sensor used, the profile area of the imaging device may be made small enough to be placed into a camera module which has a very small diameter.

This invention has been described in detail with reference to particular embodiments thereof, but it will be understood that various other modifications can be effected within the spirit and scope of this invention.

What is claimed is:

1. In a PDA having capability to transmit data between a personal computer connected to a communications network, the improvement comprising:

a video system integral with said PDA for receiving and transmitting video images, and for viewing said video images, said video system comprising;

a camera module housing an image sensor therein, said image sensor lying in a first plane and including an array of CMOS pixels for receiving images thereon, said image sensor further including circuitry means on said first plane and coupled to said array of CMOS pixels for timing and control of said array of CMOS pixels, said image sensor producing a pre-video signal, a first circuit board lying in a second plane and electrically coupled to said image sensor, said first circuit board including circuitry means for converting said pre-video signal to a desired video format;

a video view screen attached to said PDA for viewing said video images, said video view screen communicating with said first circuit board, and displaying video images processed by said first circuit board.

2. A device, as claimed in claim 1, wherein:

said first circuit board is placed adjacent said image sensor within said camera module.

3. A device, as claimed in claim 1, wherein:

said first circuit board is remote from said image sensor and placed within a housing of said PDA.

4. A device, as claimed in claim 1, wherein:

said image sensor defines a profile area in said first plane, and said first circuit board is positioned in longitudinal alignment with said image sensor such that said first circuit board does not extend substantially beyond said profile area.

5. A device, as claimed in claim 1, further including:

a second circuit board electrically coupled with said first circuit board and said image sensor for further processing said pre-video signal, said second board being placed adjacent said first circuit board within said camera module.

6. A device, as claimed in claim 1, wherein:
said first and second planes are offset from and substantially parallel to one another.

7. A device, as claimed in claim 5, wherein:
said second circuit board lies in a third plane which is offset from and extends substantially parallel to said first and second planes.

8. A device, as claimed in claim 5, wherein:
said second circuit board includes means for digital signal processing enabling the pre-video signal conditioned by said first circuit board to be viewed by said video view screen.

9. A device, as claimed in claim 1, wherein:
said first circuit board converts said pre-video signal to a post-video signal for direct reception by a remote video device, said post-video signal being of a format selected from the group consisting of a NTSC/PAL video signal and a VGA video signal.

10. A device, as claimed in claim 1, wherein:
said array of CMOS pixels includes an array of passive CMOS pixels, wherein individual passive CMOS pixels of said array of passive CMOS pixels each include a photo diode for producing photoelectrically generated signals, and an access transistor communicating with said photo diode to control the release of photoelectrically generated signals.

11. A device, as claimed in claim 1, wherein:
individual pixels within said array of CMOS pixels each include an amplifier.

12. A device, as claimed in claim 1, further including:
a retractable cable interconnecting said camera module to said PDA, said retractable cable enabling said camera module to be pulled away from said PDA for selective taking of images by said camera module, and allowing said camera module to be stored within said PDA by retracting said cable and securing said camera module within said PDA.

13. A device, as claimed in claim 1, wherein:
said PDA includes a text screen mounted therein for viewing text which is manipulated by a user.

14. A device as claimed in claim 1, further including:
a wireless telephone attached to said PDA.

15. A device, as claimed in claim 1, further including:
a remote video device electrically coupled to said video system for further viewing said video images.

16. A device, as claimed in claim 15, wherein:
said remote video device is selected from the group consisting of a television and a computer monitor.

17. In a PDA having capability to transmit data between a computer connected to a communications network, the PDA having a housing, and a video view screen for viewing the data which includes video signals, the improvement comprising:
a camera module for taking video images, said camera module communicating with circuitry within said PDA enabling viewing on said video view screen and enabling video signals to be transmitted from said camera module to said computer, said camera module including an image sensor housed therein, said image sensor lying in a first plane and including an array of CMOS pixels for receiving images thereon, said image sensor further including circuitry means on said first plane and coupled to said array of said CMOS pixels for timing and control of said array of CMOS pixels, said image sensor producing a pre-video signal; and
a first circuit board electrically connected to said image sensor and separated from said image sensor, said first circuit board including circuitry means for converting said pre-video signal to a desired video format.

18. A device, as claimed in claim 17, wherein:
said first circuit board is placed adjacent said image sensor within said camera module.

19. A device, as claimed in claim 17, wherein:
said first circuit board is placed within said housing of said PDA.

20. A device, as claimed in claim 17, wherein:
said image sensor defines a profile area in said first plane, and said first circuit board is positioned in longitudinal alignment with said image sensor such that said first circuit board does not extend substantially beyond said profile area.

21. A device, as claimed in claim 17, further including:
a second circuit board electrically coupled with said first circuit board and said image sensor for further processing said pre-video signal, said second board being placed adjacent said first circuit board within said camera module.

22. A device, as claimed in claim 17, wherein:
said first and second planes are offset from and substantially parallel to one another.

23. A device, as claimed in claim 17, wherein:
said second circuit board lies in a third plane which is offset from and extends substantially parallel to said first and second planes.

24. A device, as claimed in claim 17, wherein:
said second circuit board includes means for digital signal processing enabling the pre-video signal conditioned by said first circuit board to be viewed by said video view screen.

25. A device, as claimed in claim 17, wherein:
said first circuit board converts said pre-video signal to a post video signal for direct reception by a remote video device, said post-video signal being of a format selected from the group consisting of a NTSC/PAL video signal and a VGA video signal.

26. A device, as claimed in claim 17, wherein:
said array of CMOS pixels includes an array of passive CMOS pixels, wherein individual passive CMOS pixels of said array of passive CMOS pixels each include a photo diode for producing photoelectrically generated signals, and an access transistor communicating with said photo diode to control the release of photoelectrically generated signals.

27. A device, as claimed in claim 17, wherein:
individual pixels within said array of CMOS pixels each include an amplifier.

28. A device, as claimed in claim 17, further including:
a retractable cable interconnecting said camera module to said PDA, said retractable cable enabling said camera module to be pulled away from said PDA for selective taking of images by said camera module, and allowing said camera module to be stored within said PDA by retracting said cable and securing said camera module within said PDA.

29. A device, as claimed in claim 17, wherein:
said PDA includes a command screen mounted therein for executing commands directed by a user.

30. A device as claimed in claim 17, further including:
a wireless telephone attached to said PDA.

31. A device, as claimed in claim 17, further including:
a remote video device electrically coupled to said PDA for further viewing said video images.

32. A device, as claimed in claim 31, wherein:
said remote video device is selected from the group consisting of a television and a computer monitor.

33. A PDA having capability for receiving and transmitting video and audio images between the PDA and a personal computer connected to a communications network, said PDA comprising:
an image sensor lying in a first plane, and an array of CMOS pixels for receiving images thereon, said image sensor further including circuitry means on said first plane and coupled to said array of CMOS pixels for timing and control of said array of CMOS pixels, said image sensor producing a pre-video signal;
a first circuit board electrically communicating with said image sensor and separated from said image sensor, said first circuit board including circuitry means for converting said pre-video signal to a desired video format;
a camera module housing said image sensor;
a transceiver/amplifier section electrically coupled to said first circuit board for transmitting, receiving, and amplifying video and audio signals;
a digital signal processor electrically coupled to said first circuit board and said transceiver/amplifier section, said digital signal processor further conditioning said pre-video signal which is first conditioned by said first circuit board, and also for conditioning video and audio signals from said transceiver/amplifier section;
a microphone electrically communicating with said digital signal processor for recording and receiving audio signals;
a speaker electrically communicating with said digital signal processor for broadcasting audio signals;
a video view screen attached to said PDA, said video view screen for selectively displaying images from said imaging device, and for selectively displaying video images received by said transceiver/amplifier section;
a video switch communicating with said first circuit board and said digital signal processor for switching video images to be viewed on said video view screen; and
a power supply mounted to said PDA for providing power thereto.

34. A device, as claimed in claim 33, wherein:
said first circuit board is placed adjacent said image sensor within said camera module.

35. A device, as claimed in claim 33, wherein:
said first circuit board is remote from said image sensor and placed within a housing of said PDA.

36. A device, as claimed in claim 33, wherein:
said image sensor defines a profile area in said first plane, and said first circuit board is positioned in longitudinal alignment with said image sensor such that said first circuit board does not extend substantially beyond said profile area.

37. A device, as claimed in claim 33, further including:
a second circuit board electrically coupled with said first circuit board and said image sensor for further processing said pre-video signal, said second board being placed adjacent said first circuit board.

38. A device, as claimed in claim 33, wherein:
said first and second planes are offset from and substantially parallel to one another.

39. A device, as claimed in claim 37, wherein:
said second circuit board lies in a third plane which is offset from and extends substantially parallel to said first and second planes.

40. A device, as claimed in claim 37, wherein:
said second circuit board includes means for digital signal processing enabling the pre-video signal conditioned by said first circuit board to be viewed by said video view screen.

41. A device, as claimed in claim 33, wherein:
said first circuit board converts said pre-video signal to a post-video signal for direct reception by a remote video device, said post-video signal being of a format selected from the group consisting of a NTSC/PAL video signal and a VGA video signal.

42. A device, as claimed in claim 33, wherein:
said array of CMOS pixels includes an array of passive CMOS pixels, wherein individual passive CMOS pixels of said array of passive CMOS pixels each include a photo diode for producing photoelectrically generated signals, and an access transistor communicating with said photo diode to control the release of photoelectrically generated signals.

43. A device, as claimed in claim 33, wherein:
individual pixels within said array of CMOS pixels each include an amplifier.

44. A device, as claimed in claim 33, further including:
a retractable cable interconnecting said imaging device to said PDA, said retractable cable enabling said imaging device to be pulled away from said PDA for selective taking of images by said imaging device, and allowing said imaging device to be stored within said PDA by retracting said cable and securing said camera module within said PDA.

45. A device, as claimed in claim 33, wherein:
said PDA includes a text screen mounted therein for viewing text which is manipulated buy a user.

46. A device as claimed in claim 33, further including:
a wireless telephone attached to said PDA.

47. A device, as claimed in claim 33, further including:
a remote video device electrically coupled to said video system for further viewing said video image.

48. A device, as claimed in claim 47, wherein:
said remote video device is selected from the group consisting of a television and a computer monitor.

49. In a PDA having capability to transmit data between a personal computer connected to a communications network, the improvement comprising:
a video system integral with said PDA for receiving and transmitting video images, and for viewing said images, said video system comprising:
a camera module housing an image sensor therein, said image sensor lying in a first plane and including an array of CMOS pixels for receiving images thereon, said image sensor producing a pre-video signal, a first circuit board lying in a second plane and electrically coupled to said image sensor, said first circuit board including circuitry means for timing and control of said array of CMOS pixels and circuitry means for processing and converting said pre-video signal to a desired video format; and
a video view screen attached to said PDA for viewing said video images, said video view screen communicating with said first circuit board.

50. A device, as claimed in claim 49, wherein:
said first circuit board is placed adjacent to said image sensor and within said camera module.

51. A device, as claimed in claim 49, wherein:
said first circuit board is remote from said image sensor and placed within a housing of said PDA.

52. In a PDA having capability to transmit data between a personal computer connected to a communications network, the improvement comprising:
a video system integral with said PDA for receiving and transmitting video images, and for viewing said images, said video system comprising:
a camera module housing an image sensor therein, said image sensor lying in a first plane and including an array of CMOS pixels for receiving images thereon, circuitry means electrically coupled to said array of CMOS pixels for timing and control of said array of CMOS pixels, said circuitry means for timing and control being placed remote from said array of CMOS pixels on a second plane, said image sensor producing a pre-video signal, a first circuit board lying in a third plane and electrically coupled to said image sensor, said first circuit board including circuitry means for processing and converting said pre-video signal to a desired video format; and
a video view screen attached to said PDA for viewing said video images, said video view screen communicating with said first circuit board, and displaying video images processed by said first circuit board.

53. A device, as claimed in claim 52, wherein:
said circuitry means for timing and control is placed adjacent to said image sensor in said camera module.

54. A device, as claimed in claim 52, wherein:
said circuitry means for timing and control is placed within a housing of the PDA.

55. In a PDA having capability to transmit data between a personal computer connected to a communications network, the PDA including a video view screen for viewing video images, the improvement comprising:
a camera module for taking video images, said camera module communicating with circuitry within said PDA enabling viewing on said video view screen and enabling video signals to be transmitted from said camera module to the personal computer, said camera module including an image sensor housed therein, said image sensor lying in a first plane and including an array of CMOS pixels for receiving images thereon, said image sensor producing a pre-video signal, a first circuit board lying in a second plane and electrically connected to said image sensor, said first circuit board including circuitry means for timing and control of said array of CMOS pixels and circuitry means for processing and converting said pre-video signal to a desired video format.

56. A device, as claimed in claim 55, wherein:
said first circuit board is placed adjacent said image sensor within said camera module.

57. A device, as claimed in claim 55, wherein:
said first circuit board is placed within a housing of said PDA.

58. In a PDA having capability to transmit data between a personal computer connected to a communications network, the PDA including a video view screen for viewing the video images, the improvement comprising:
a camera module for taking video images, said camera module communicating with circuitry within said PDA enabling viewing of said video images on said PDA and enabling video signals to be transmitted from said camera module to the personal computer, said camera module including an image sensor housed therein, said image sensor lying in a first plane and including an array of CMOS pixels for receiving images thereon, said image sensor further including circuitry means electrically coupled to said array of said CMOS pixels for timing and control of said array of CMOS pixels, said circuitry means for timing and control placed remote from said array of CMOS pixels on a second plane, said image sensor producing a pre-video signal, a first circuit board electrically connected to said image sensor and lying in a third plane, said first circuit board including circuitry means for processing and converting said pre-video signal to a desired video format.

59. A device, as claimed in claim 58, wherein:
said circuitry means for timing and control is placed adjacent to said image sensor in said camera module.

60. A device, as claimed in claim 58, wherein:
said circuitry means for timing and control is placed within a housing of said PDA.

61. A PDA having capability for receiving and transmitting video and audio images between the PDA and a personal computer connected to a communications network, said PDA comprising:
an image sensor lying in a first plane including an array of CMOS pixels for receiving images thereon, said image sensor producing a pre-video signal;
a first circuit board electrically communicating with said image sensor and separated from said image sensor, said first circuit board including circuitry means for timing and control of said array of CMOS pixels and circuitry means for processing and converting said pre-video signal to a desired video format;
a camera module housing said image sensor;
a transceiver/amplifier section electrically coupled to said first circuit board for transmitting, receiving, and amplifying video and audio signals;
a digital signal processor electrically coupled to said first circuit board and said transceiver/amplifier section, said digital signal processor further conditioning said pre-video signal which is first conditioned by said first circuit board, and also for conditioning video and audio signals from said transceiver/amplifier section;
a microphone electrically communicating with said digital signal processor for recording and receiving audio signals;
a speaker electrically communicating with said digital signal processor for broadcasting audio signals;
a video view screen attached to said PDA, said video view screen for selectively displaying images from said imaging device, and for selectively displaying video images received by said transceiver/amplifier section;
a video switch communicating with said first circuit board and said digital signal processor for switching video images to be viewed on said video view screen; and
a power supply mounted to said PDA for providing power thereto.

62. A device, as claimed in claim 61, wherein:
said first circuit board is placed adjacent to said image sensor and within said camera module.

63. A device, as claimed in claim 61, wherein:
said first circuit board is remote from said image sensor, and placed within a housing of said PDA.

64. A PDA having capability for receiving and transmitting video and audio images between the PDA and a personal computer connected to a communications network, said PDA comprising:

an image sensor lying in a first plane, and an array of CMOS pixels for receiving images thereon, said image sensor further including circuitry means electrically coupled to said array of CMOS pixels for timing and control of said array of CMOS pixels, said circuitry means for timing and control being placed remote from said array of CMOS pixels on a second plane, said image sensor producing a pre-video signal;

a first circuit board electrically coupled with said image sensor and lying in a third plane, said first circuit board including circuitry means for processing and converting said pre-video signal to a desired video format;

a camera module housing said image sensor;

a transceiver/amplifier section electrically coupled to said first circuit board for transmitting, receiving, and amplifying video and audio signals;

a digital signal processor electrically coupled to said first circuit board and said transceiver/amplifier section, said digital signal processor further conditioning said pre-video signal which is first conditioned by said first circuit board, and also for conditioning video and audio signals from said transceiver/amplifier section;

a microphone electrically communicating with said digital signal processor for recording and receiving audio signals;

a speaker electrically communicating with said digital signal processor for broadcasting audio signals;

a video view screen attached to said PDA, said video view screen for selectively displaying images from said imaging device, and for selectively displaying video images received by said transceiver/amplifier section;

a video switch communicating with said first circuit board and said digital signal processor for switching video images to be viewed on said video view screen; and a power supply mounted to said PDA for providing power thereto.

65. A device, as claimed in claim 64, wherein:
said circuitry means for timing and control is placed adjacent to said image sensor in said camera module.

66. A device, as claimed in claim 65, wherein:
said circuitry means for timing and control is placed within a housing of said PDA.

67. In a method for conducting video conferencing communications through connection with a communications network, the improvement comprising the steps of:
providing a camera module having an image sensor housed therein;
providing a flexible cable for interconnecting the camera module to a PDA;
displacing the camera module away from the PDA;
pointing the camera module at a targeted object; and
taking video images of the targeted object by the camera module for viewing on the PDA, and for transmission of the video images to the communications network.

68. A method, as claimed in claim 67, further comprising the steps of:
selectively extending and selectively retracting the cable, enabling the camera module to be pointed in a desired direction toward the targeted object.

69. A method, as claimed in claim 67, wherein:
said image sensor includes a CMOS pixel array.

70. In a PDA having capability for data exchange between a personal computer connected to a communications network, the improvement comprising:
a camera module housing an image sensor therein, said camera module for producing video images of a targeted object;
means for interconnecting said camera module to said PDA, said means for interconnecting including a flexible cable enabling said camera module to be selectively displaced at a location remote from said PDA; and
a video view screen attached to said PDA for selectively viewing video images taken by said camera module, and for selectively viewing incoming video images received from the personal computer connected to the communications network.

71. A device, as claimed in claim 70, wherein:
said PDA includes a housing, and an opening for receiving said camera module so as to place said camera module in a stored position.

72. In a PDA having a housing and a video view screen for viewing video images, the improvement comprising:
a camera module housing an image sensor therein, said camera module for producing video images of a targeted object; and
means for interconnecting said camera module to said PDA, said means for interconnecting including a flexible cable enabling said camera module to be selectively displaced at a location remote from said PDA.

73. A device, as claimed in claim 72, wherein:
said PDA includes an opening in said housing for receiving said camera module so as to place said camera module in a stored position.

74. In a PDA, the improvement comprising:
a camera module housing an image sensor therein;
circuitry means coupled to said image sensor for timing and control of said image sensor;
circuitry means for processing images taken by said image sensor to create video signals of a desired video format;
means for interconnecting said camera module to a housing of said PDA, said means for interconnecting including a flexible connection enabling said camera module to be selectively displaced at multiple angles from said housing by the user for pointing the camera module at a targeted object, and enabling said camera module to be retracted for movement back to said housing.

75. A device, as claimed in claim 74, wherein:
said PDA includes an opening in said housing for receiving said camera module so as to place said camera module in a stored position.

* * * * *